United States Patent
Mack

(10) Patent No.: US 6,733,969 B2
(45) Date of Patent: *May 11, 2004

(54) EXPRESSION MONITORING FOR GENE FUNCTION IDENTIFICATION

(75) Inventor: David H. Mack, Menlo Park, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/836,278

(22) Filed: Apr. 18, 2001

(65) Prior Publication Data

US 2002/0028454 A1 Mar. 7, 2002

Related U.S. Application Data

(60) Division of application No. 09/086,285, filed on May 29, 1998, now Pat. No. 6,303,301, which is a continuation-in-part of application No. PCT/US98/01206, filed on Jan. 12, 1998.
(60) Provisional application No. 60/035,327, filed on Jan. 13, 1997.

(51) Int. Cl.[7] .......................... C07H 21/04; C12Q 1/68
(52) U.S. Cl. .......................... 435/6; 435/91.2; 536/23.1
(58) Field of Search .......................... 435/6, 91.1, 91.2; 536/23.1

(56) References Cited

U.S. PATENT DOCUMENTS

| | | | | |
|---|---|---|---|---|
| 5,807,522 A | * | 6/1995 | Brown et al. .................. | 435/6 |
| 5,700,637 A | | 12/1997 | Southern | |
| 6,020,135 A | * | 2/2000 | Levine et al. .................. | 435/6 |
| 6,177,248 B1 | * | 1/2001 | Oliner et al. .................. | 435/6 |
| 6,258,536 B1 | * | 7/2001 | Oliner et al. .................. | 435/6 |
| 6,303,301 B1 | * | 10/2001 | Mack .......................... | 435/6 |

FOREIGN PATENT DOCUMENTS

| | | | |
|---|---|---|---|
| WO | 89/10977 | 11/1989 | |
| WO | WO 92/10588 | 6/1992 | ............ C12Q/1/68 |

OTHER PUBLICATIONS

Sanchez–Beato et al. J. Pathology (1996) 180:58–64.*
Velculescu et al. Clinical Chemistry (1996) 6: 858–868.*
Lewin. Genes V 1994, p. 76.*
Sanchez–Beato et al. "MDM2 and p21, wild–type p53–induced proteins are regularly expressed by stemberred cells in hodgkins disease" 1996, Journal of Pathology, 180:58–64.
Lewin, B. Genes V, 1994, p. 76.
Schena et al. Parallel human genome analysis. Proc. Natl. Acad. Sci. 93(20):10614–10619, Oct. 1996.
Velculescu et al. Biological & Clinical Importance of p53 Clinical Chemistry Vo. 6, 858–868, 1996.
Lipshutz et al. Using Oligonucleotide Probe Arrays to Access Genetic Diversity, BioTechniques, Sep. 1995, vol. 19, No. 3, pp. 442–447.

Drmanac et al. Gene–Representing cDNA Clusters Defined by Hybridization of 57,419 Clones from Infant Brain Libraries with Short Oligonucleotide Probe, Genomics, Oct. 1, 1996, vol. 37, No. 1, pp. 29–40.
Chee et al. Accessing Genetic Information with High–Density DNA Arrays, Science, Oct. 5, 1996, vol. 274, No. 5287, pp. 610–614.
Geoffrey J. Clark et al. "Aberrant function of the Ras signal transduction pathway in human breast cancer" Breast Cancer Research and Treatment 35: 133–144 1995.
Nature Genetics ISSN 1061–4036 Nature Publishing Company, 1993, vol. 4, pp. 332–333.
Dennis J. Slamon et al. "Human Breast Cancer: Correlation of Relapse and Survival with Amplification of the HER–2/neu Oncogene" Science ISSN 0036–8076 Elsevier Science 1987 vol. 4785, pp. 177–182.
March Chee et al. "Accessing Genetic Information with High–Density DNA Arrays" Science, ISSN 0036–8075 Elsevier Science, 1996, vol. 5287, pp. 610–614.
Lisa Coussens et al. "Tyrosine Kinase Receptor with Extensive Homology to EGF Receptor Shares Chromosomal Location with neu Oncogene" Science ISSN 0036–8075 Elsevier Science, 1985, vol. 4730, pp. 1132–1139.
C. Richter King et al. "Amplification of a Novel v–erb-B–Related Gene in a Human Mammary Carcinoma" Science, ISSN 0036–8075 Elsevier Science, 1985, vol. 4717, pp. 974–976.
Dennis J. Slamon et al. "Studies of the HER–2/neu Proto–oncogene in Human Breast and Ovarian Cancer" Science, ISSN 0036–8075 Elsevier Science, 1989, vol. 4905, pp. 707–712.
Tim van Blesen et al. "Receptor–tyrosine–kinase– and Gβγ–mediated MAP kinase activation by a common signaling pathway", Nature, ISSN 0028–0836 MacMillan Journals 1995, vol. 6543, pp. 781–784.
N. Li et al. "Guanine–nucleotide–releasing factor hSos1 binds to Grb2 and links receptor tyrosine kinases to Ras signalling" Nature ISSN 0028–0836 MacMillan Journals, 1993, vol. 6424, pp. 85–88.

(List continued on next page.)

Primary Examiner—Gary Benzion
Assistant Examiner—Jeanine Goldberg
(74) Attorney, Agent, or Firm—Banner & Witcoff, Ltd.

(57) ABSTRACT

This invention provides methods, compositions and apparatus for mapping the regulatory relationship among genes by massive parallel monitoring gene expression. In some embodiments, mutations in the up-stream regulatory genes are detected by monitoring the change in down-stream gene expression. Similarly, the function of a specific mutation in a up-stream gene is determined by monitoring the down-stream gene expression. In addition, regulatory function of a target gene can be determined by monitoring the expression of a large number of down-stream genes. The invention also provides specific embodiments for detecting p53 functional homozygous and heterozygous mutations and for determining the function of p53 mutations.

15 Claims, 21 Drawing Sheets

OTHER PUBLICATIONS

Matthias H. Kraus et al. "Isolation and characterization of ERBB3, a third member of the ERBB/epidermal growth factor receptor family: Evidence for overexpression in a subset of human mammary tumors" PNAS—Proceedings of the National Academy of Sciences, ISSN 0027–8424 National Academy of Sciences, 1989, vol. 23, pp. 9193–9197.

Anthonly J. Koleske et al. "Reduction of cavolin and caveolae in oncogenically transformed cells" PNAS—Proceedings of the National Academy of Sciences, ISSN 0027–8424 National Academy of Sciences, 1995, vol. 92, pp. 1381–1385.

N.R. Lemoine et al. "Expression of the ERBB3 gene product in breast cancer" British Journal of Cancer, 1992, vol. 66, pp. 1116–1121.

H. Skhelton et al. "Heterodimerization and functional interaction between EGF receptor family members: A new signaling paradign with implications for breast cancer research" Breast Cancer Research and Treatment ISSN 0107–8606 The Hague; Boston; M. Nijhoff 1995, vol. 35, pp. 115–132.

D. Stein et al. "The SH2 domain protein GRB–7 is co–amplified, overexpressed and in a tight complex with HER2 in breast cancer" EMBO Journal, ISSN 0261–4189 Oxford University Press, 1994, vol. 13, pp. 1331–1340.

Shengwen Li et al. "Evidence for a Regulated Interaction between Heterotrimeric G Proteins and Caveolin" Journal of Biological Chemistry ISSN 0021–9258 American Society of Biological Cheemists 1995, vol. 26, pp. 15693–15701.

Louis R. Howe et al. "Lysophosphatidic Acid Stimulates Mitogen–activated Protein Kinase Activation via a G–protein–coupled Pathway Requiring p21 and p74 " Journal of Biological Chemistry, ISSN 0021–9258 American Society of Biological Chemists 1993, vol. 28, pp. 20717–20720.

Jacqueline Alblas et al. "G1–mediated Activation of the p21ras–Mitogen–activated protein Kinase Pathway by α2–Adrenergic Receptors Expressed in Fibroblasts" Journal of Biological Chemistry ISSN 0021–9258 American Society of Biological Chemistrs 1993 vol. 30 pp. 22235–22238.

Michael P. Lisant "Caveolae, transmembrane signaling and cellular transformation" Molecular membrane biology, ISSN 0968–7688 Taylor & Francis, 1995, vol. 1, pp. 121–124.

Christian Wallasch et al. "Heregulin–dependent regulation of HER2/neu oncogenic signaling by heterodimerization with HER3" EMBO Journal, ISSN 0261–4189 Oxford University Press, 1995, vol. 14, pp. 4267–4275.

Rony Seger et al. "The MAPK signaling cascade" Faseb Journal, ISSN 0892–6638 Rossenfa and Labeur 1995, vol. 9, pp. 726–735.

Victor E. Velculescu et al. "Biological and clinical importance of the p53 tumor suppressor gene" Clinical chemistry ISSN 0009–9147 P.B. Hoeber 1996 vol. 6, pp. 858–868.

Adeline J. Hackett et al. "Two Syngeneic Cell Lines form Human Breast Tissue: The Aneuploid Mammary Epithelial (Hs578t) and the Diploid Myoepithelia (Hs578st) Cell Lines" Journal of the National Cancer Institute ISSN 0027–8874 Department of Health and Human Services, 1977, vol. 58(6) pp. 1795–1806.

Etienne Y. Lasfargues et al. "Isolation of Two Human Tumor Epithelia Cell Lines from Solid Breast Carcinomas" Journal of the National Cancer Institute, ISSN 0027–8874 Department of Health & Human Services, 1978, vol. 61(4) pp. 967–978.

March Schena et al. "Quantitative Monitoring of Gene Expression Patterns with a Complementary DNA Microarray" Science, ISSN 0036–8075, Elsevier Science, 1995, pp. 467–470.

Jennefit M. Styles et al. "Rath Monoclonal Antibodies to the External Domain of the Product of the C–erB–2 Proto–Oncogene" International Journal of Cancer ISSN 0020–7136 Alan R. Liss, Inc. 1990 V. 45(2) pp. 320–324.

David J. Lockhart "Expression monitory by hybridization to high–density oligonucleotide arrays" Nature biotechnology, 1996, pp. 1675–1680.

Mark S. Marshal "Ras target proteins in eukaryotic cells" Faseb Journal ISSN 0892–6638 Rossenfa and Labeur 1995, vol. 9(13), pp. 1311–1318.

Victor E. Velculescu et al. "Serial Analysis of Gene Expression" Science, vol. 270, Oct. 20, 1995, pp. 484–487.

Arnold J. Levine et al. "p53, the Cellular Gatekeeper for Growth and Division" Cell, vol. 88, pp. 323–331, Feb. 7, 1997.

Stuart G. Lutzker et al. "A functionally inactive p53 protein in tetratocarcinoma cells is activated by either DNA damage of cellular differentiation" Nature Medicine, vol. 2, No. 7, Jul. 1996, pp. 804–810.

P.M. Bentler "Multivariate Analysis with Latent Variables: Causal Modeling" Ann. Rev. Psychol. 1980, 31:419–56 The Journal of NIH Research, Jan. 1997, vol. 9, "To Much Information? Making Sense of Genome Sequence", pp. 23–27.

Jackson S. Wan et al. "Cloning differentially expressed mRNAs" Nature Biotechnology, vol. 14, Dec. 1996, pp. 1685–1691.

Mark D. Adams et al. "Initial assessment of human gene diversity and expression patterns based upon 83 million nucleotides of cDNA sequence" Nature ISSN 0028–0836 MacMillan Journals 1995, vol. 377 (6547 Suppl) pp. 3–174.

* cited by examiner

FIG. 10A

Table 3.

Genes transcriptionally induced in BT-474 vs HT-125

| Accession | | Functional category |
|---|---|---|
| *Nominal copy number: 500~1,000 copies/cell* | | |
| X00474 | PS2 protein precursor | other |
| M11730 | Her2/neu tyrosine kinase receptor | signal transduction |
| R10066 | cDNA clone 128808 similar to Prohibitin | other |
| | | |
| *Nominal copy number: 100-500 copies/cell* | | |
| J05068 | Transcobalamin I | other |
| M22382 | Mitochondrial matrix protein P1 precursor | mitochondrial |
| T54303 | cDNA clone 69022 similar to Keratin, type II cytoskeletal 8 | structural/cytoskeletal |
| L33930 | CD24 | signal transduction |
| T51499 | cDNA clone 71494 similar to Succinate dehydrogenase | metabolic enz. |
| T70062 | cDNA clone 80945 similar to NF45 | transcription factor |
| X70940 | Elongation factor 1 alpha-2 | translational mach. |
| M88279 | Human immunophilin | other |
| D45370 | Adipose specific protein | other |
| H52207 | cDNA clone 209710 similar to Matrix GLA-protein precursor | other |
| L08044 | Intestinal trefoil factor | secr. gr. fact. |
| M31627 | X Box binding protein-1 | transcription factor |
| U37519 | Aldehyde dehydrogenase | metabolic enz. |
| U39840 | Hepatocyte nuclear factor-3 alpha | transcription factor |
| M26481 | KS1/4 antigen | other |
| H09351 | cDNA clone 46019 similar to MCM3 homolog | DNA replication |
| T51961 | Proliferating cell nuclear antigen | DNA replication |
| T59162 | cDNA clone 74635 similar to Selenium-binding protein | other |

FIG. 10B

Nominal copy number: 50-100 copies/cell

| | | |
|---|---|---|
| T67986 | cDNA clone 82030 similar to Clusterin precursor | cell ad./cell-cell comm. |
| U21931 | Fructose-1,6-biphosphatase | metabolic enz. |
| Z13009 | E-cadherin | cell ad./cell-cell comm. |
| M18216 | Nonspecific crossreacting antigen | other |
| U31875 | Hep27 protein | other |
| L02547 | Cleavage stim.factor | translational mach. |
| R89566 | cDNA clone 195338 similar to lamin B receptor | other |
| T98835 | cDNA clone 122341 similar to 80.7 KD alpha trans-inducing protein | other |
| R00451 | cDNA clone 123283 similar to Clathrin coat assembly protein AP47 | other |
| M34309 | Human epidermal growth factor receptor, HER3 | signal transduction |
| X73424 | Propionyl-COA carboxylase beta chain | metabolic enz. |
| X89985 | BCL7B | other |
| H00645 | cDNA clone 149859 similar to Ribonuclease inhibitor | other |
| H41017 | cDNA clone 192957 similar to Creatine kinase, ubiquitous mitochondrial precursor | mitochondrial |
| R85558 | cDNA clone 180221 similar to Inorganic pyrophosphatase | metabolic enz. |

Nominal copy number: 10-50 copies/cell

| | | |
|---|---|---|
| H41006 | cDNA clone 177323 similar to Quinol oxidase polypeptide I | other |
| X51801 | OP-1, osteogenic protein | secr. gr. fact. |
| M69238 | Aryl hydrocarbon receptor nuclear translocator | transcription factor |
| X69392 | Ribosomal protein L26. | translational mach. |

FIG. 10C

| Accession | Description | Category |
|---|---|---|
| R88418 | cDNA clone 166353 similar to Cleavage stimulation factor, 50 KD subunit | translational mach. |
| Y00815 | Leukocyte antigen related protein | cell ad./cell-cell comm. |
| H41406 | cDNA clone 192943 similar to mouse Gamma-adaptin | protein process. |
| X92814 | HREV107-like protein. | other |
| X68194 | h-Sp1 | other |
| R42070 | cDNA clone 30646 similar to Verprolin | structural/cytoskeletal |
| H19467 | cDNA clone 172249 similar to Ankyrin R | other |
| R10620 | cDNA clone 128901 similar to Tyrosine-protein kinase CSK | signal transduction |
| L29254 | L-iditol-2 dehydrogenase gene | metabolic enz. |
| M34458 | Lamin B1 | other |
| R53942 | cDNA clone 40026 similar to ADP,ATP carrier protein, heart/skeletal muscle isoform | other |
| T96666 | cDNA clone 121357 similar to Cyclin-dependent kinase interactor 1 | cell-cycle |
| R44863 | cDNA clone 33477 similar to Phenylalkylamine binding protein | other |
| D43772 | GRB-7 | signal transduction |
| X67334 | BM28 | DNA replication |
| T78606 | cDNA clone 113492 similar to Translational activator GCN1 | translational mach. |
| D42047 | KIAA0089 Human mRNA gene for Mouse glycerophosphate dehydrogenase-related | metabolic enz. |
| X58072 | hGATA3 | transcription factor |
| M34344 | Platelet glycoprotein IIb | cell ad./cell-cell comm. |
| R46731 | cDNA clone 36517 similar to Transcriptional regulatory protein RPD3 | transcriptional mach. |
| U33819 | Zinc-finger DNA binding protein | transcription factor |
| R23246 | cDNA clone 131094 similar to Goliath protein | other |
| H64489 | cDNA clone 238846 similar to Leukocyte antigen CD3 | cell ad./cell-cell comm. |
| T47377 | cDNA clone 571035 similar to S-100P protein | other |

FIG. 10D

| | | |
|---|---|---|
| H05814 | cDna clone 44151 similar to Putative ATP-dependent RNA helicase | translational mach. |
| X83618 | 3-hydroxy-3-methylglutaryl coenzyme A synthase | metabolic enz. |
| U14550 | Sialyltransferase SThM | metabolic enz. |
| R55185 | cDNA clone 154654 similar to Galactoside 3(4)-L-fucosyltransferase | metabolic enz. |
| V00568 | C-myc | transcription factor |
| L47738 | Inducible protien | other |
| M20560 | Lipocortin-III | other |
| T47964 | cDna clone 71549 similar to Purine nucleoside phosphorylase | metabolic enz. |
| T90192 | cDna clone 110564 similar to DNA-binding protein MEL-18 | transcription factor |
| U20285 | GPS1 | signal transduction |
| M81637 | Grancalcin | other |
| H19201 | cDna clone 508873 similar to Guanine nucleotide diss. stim. | signal transduction |
| X03635 | Oestrogen receptor | transcription factor |
| X52426 | Cytokeratin 13 | structural/cytoskeletal |
| R37799 | cDNA clone 270833 similar to Protein phosphatase PP2A | signal transduction |
| X03484 | Raf oncogene | signal transduction |
| L11284 | ERK activator kinase, MEK1 | signal transduction |
| X70683 | SOX-4 | transcription factor |
| R72644 | cDna clone 156489 3' similar to Choline kinase | other |
| M97370 | Adenosine receptor (A2) | signal transduction |
| X76180 | Lung amiloride sensitive Na+ channel protein | cell ad./cell-cell comm. |
| R45583 | cDNA clone 35271 similar to NG-CAM related cell adhesion molecule | cell ad./cell-cell comm. |
| M13665 | C-myb | transcription factor |
| D26018 | Human mRNA (KIAA0039) for ORF | other |
| H54752 | cDna clone 203275 similar to Activator 1 37 KD subunit | other |
| H04239 | cDna clone 151776 similar to Developmental protein seven in absentia | signal transduction |

FIG. 10E

| Accession | Description | Category |
|---|---|---|
| D21852 | Human mRNA (KIAA0029) for ORF | other |
| M57730 | Immediate early response protein B61 precursor | secr. gr. fact. |
| M16768 | Human T-cell receptor gamma chain VJCI-CII-CIII region | other |
| X13956 | 12S RNA induced by poly(rI), poly(rC) and Newcastle disease virus | other |
| U07349 | Human B lymphocyte serine/threonine protein kinase | signal transduction |
| D00726 | Ferrochelatase | metabolic enz. |
| M54968 | K-ras oncogene | signal transduction |
| D31661 | ERK tyrosine kinase | signal transduction |
| U21108 | Human dual specific protein phosphatase | signal transduction |
| X52228 | Secreted epithelial tumour mucin antigen | other |
| X13425 | Pancreatic carcinoma marker GA733-1 | other |
| R52511 | cDNA clone 39763 similar to Gamma-interferon-inducible protein IP-30 precursor | other |
| X83425 | Lutheran blood group glycoprotein. | cell ad./cell-cell comm. |
| U13045 | Human nuclear respiratory factor-2 subunit beta 1 | transcription factor |
| M20132 | Androgen receptor | transcription factor |
| L07615 | Neuropeptide Y receptor Y1 | signal transduction |
| M86699 | Human kinase, TTK | signal transduction |
| R43936 | cDNA clone 32974 similar to Serine/threonine-protein kinase STE20 | signal transduction |
| X60787 | Transcription factor ILF | transcription factor |
| X74570 | Gal-beta(1-3/1-4)GlcNAc alpha-2,3-sialyltransferase | metabolic enz. |
| U30255 | Pphosphogluconate dehydrogenase | metabolic enz. |
| D11466 | For Pig N-acetylglucosaminyl-phosphatidylinositol | other |
| M64347 | Novel growth factor receptor | signal transduction |
| R43064 | cDNA clone 32719 similar to E2 protein | transcription/replication |
| M60724 | p70 ribosomal S6 kinase alpha-1 | translational mach. |
| U34074 | A kinase anchor protein S-AKAP84 | mitochondrial |
| H87205 | cDNA clone 220505 similar to cell division protein kinase 5 | cell-cycle |
| X57348 | cDNA clone 9112 similar to H.sapiens mRNA | other |
| X07696 | Keratin, type I cytoskeletal 15 | structural/cytoskeletal mach. |
| X13482 | U2 small nuclear ribonucleoprotein A' | translational mach. |

FIG. 10F

| Accession | Nominal copy number: 1-10 copies/cell | Category |
|---|---|---|
| D63879 | Human mRNA for ORF (KIAA0196) | other |
| M90656 | Gamma-glutamylcysteine synthetase (GCS) | metabolic enz. |
| H13822 | cDNA clone 148291 similar to Zinc finger autosomal protein | other |
| X83928 | Transcription factor TFIID subunit TAFII28 | transcriptional mach. |
| H52655 | cDNA clone 235891 similar to DNA polymerase beta | DNA replication |
| R42095 | Tyrosine kinase SEK receptor precursor | signal transduction |
| D13633 | Human mRNA for ORF (KIAA008) | other |
| U13616 | Human ankyrin G | other |
| M74558 | SIL mRNA | other |
| X63468 | Transcription factor TFIIE alpha | transcriptional mach. |
| M30704 | Amphiregulin | other |
| U11700 | Copper transporting ATPase | metabolic enz. |
| H78807 | cDNA clone 230127 similar to D-beta-hydroxybutyrate dehydrogenase precursor | metabolic enz. |
| M58411 | p80-coilin | translational mach. |
| U25975 | Serine kinase, hPAK65 | signal transduction |
| R42898 | cDNA clone 32410 similar to JNK activating kinase 1 | signal transduction |
| J03258 | Vitamin D3 receptor | signal transduction |

FIG. 10G

Genes transcriptionally repressed in BT-474 vs HT-125

| Accession | | Functional category |
|---|---|---|
| | Nominal copy number: 500-1,000 copies/cell | |
| H41129 | cDNA clone 175539 similar to Galectin-1 | cell ad./cell-cell comm. |
| T51261 | cDNA clone 70133 similar to Glia derived nexin precursor | protein process. |
| | Nominal copy number: 100-500 copies/cell | |
| R91912 | Placental calcium-binding protein | other |
| M77349 | Transforming growth factor-beta induced gene product | other |
| M35878 | Clone HL 1006d similar to IGFBP3 | other |
| T92451 | cDNA clone 118219 similar to Tropomyosin | structural/cytoskeletal |
| M95787 | Smooth muscle protein 22-alpha | structural/cytoskeletal |
| J03210 | Collagenase type IV mRNA, 3' end. | ECM |
| L16895 | Human lysyl oxidase | cell ad./cell-cell comm. |
| X57351 | Interferon-inducible protein 1-8D | other |
| T99774 | cDNA clone 122884 similar to Follistatin precursor | cell ad./cell-cell comm. |
| J03464 | Clone pHcol2A1 similar to Procollagen alpha 2(I)chain precursor | ECM |
| T61333 | cDNA clone 78034 similar to Metalloproteinase inhibitor 3 precursor | protein process. |
| X78947 | Connective tissue growth factor | secr. gr. fact. |
| R49855 | cDNA clone 152637 similar to Coagulation factor V precursor | other |
| T54767 | cDNA clone 73802 similar to Sparc precursor | cell ad./cell-cell comm. |
| L01131 | Human decorin | cell ad./cell-cell comm. |
| L16510 | Cathepsin B | protein process. |
| H87343 | cDNA clone 252394 similar to Protein-lysine 6-oxidase precursor | protein process. |
| M69066 | Moesin | structural/cytoskeletal |
| X91911 | RTVP-1 | other |
| T95046 | cDNA clone 120085 similar to Protease do precursor | protein process. |
| X15882 | Collagen VI alpha-2 C-terminal globular domain. | structural/cytoskeletal |
| M69054 | IGFBP6 | other |
| X55740 | Placental cDNA coding for 5' nucleotidase | metabolic enz. |
| H80342 | cDNA clone 241122 similar to Tubulin beta chain | structural/cytoskeletal |
| U21090 | DNA polymerase delta | DNA replication |
| Z18951 | Caveolin-1 | signal transduction |

FIG. 10H

Nominal copy number: 50-100 copies/cell

| | | |
|---|---|---|
| U39050 | Human mitogen-responsive phosphoprotein | other |
| H62466 | cDNA clone 209654 similar to Collagen alpha 3(VI) chain | structural/cytoskeletal |
| X14787 | Thrombospondin | cell ad./cell-cell comm. |
| H45474 | cDNA clone 183508 similar to Peripheral myelin protein 22 | signal transduction |
| H29761 | cDNA clone 186308 similar to Annexin I | cell ad./cell-cell comm. |
| M11718 | Alpha-2 type V collagen | structural/cytoskeletal |
| X12369 | Tropomyosin alpha chain, smooth muscle | structural/cytoskeletal |
| T54317 | cDNA clone 69040 similar to RAS-related protein | signal transduction |
| U20280 | Cathepsin X | protein process. |
| H23235 | cDNA clone 52096 similar to APDGFR precursor | signal transduction |
| R67072 | cDNA clone 140763 similar to GAP junction alpha-1 protein | cell ad./cell-cell comm. |
| R72104 | cDNA clone 155771 similar to Bone morphogenetic protein 1 precursor | protein process. |
| U21128 | Lumican | ECM |

FIG. 10I

| | | |
|---|---|---|
| M23419 | Initiation factor 5A | translational mach. |
| L34056 | Cadherin-11 | signal transduction |
| M64110 | Caldesmon | structural/cytoskeletal |
| X72012 | Endoglin | signal transduction |
| R70383 | cDNA clone 155241 similar to Vitellogeinin II precursor | other |
| T69425 | cDNA clone 82963 similar to Alpha-2 macroglobulin precursor | other |
| H02540 | cDNA clone 151270 similar to Cathepsin L precursor | protein process. |
| X05232 | Stromelysin | protein process. |
| T54278 | cDNA clone 69199 similar to Tissue inhibitor of metalloproteinases II precursor | protein process. |
| M24486 | Prolyl 4-hydroxylase alpha subunit | ECM |
| H80975 | cDNA clone 240954 similar to Plasma protease C1 inhibitor precursor | protein process. |
| H06706 | cDNA clone 44616 similar to RAS-related protein ORAB-1 | signal transduction |
| M33210 | Colony stimulating factor 1 receptor | signal transduction |
| T96364 | cDNA clone 121066 similar to M-phase inducer phosphatase 3 | metabolic enz. |

FIG. 10J

Nominal copy number: 10-50 copies/cell

| Accession | Description | Category |
|---|---|---|
| J02814 | Chondroitin sulfate proteoglycan core protein | cell ad./cell-cell comm. |
| D14874 | Adrenomedullin | other |
| L35594 | Autotaxin | cell ad./cell-cell comm. |
| R23249 | cDNA clone 131100 similar to Preprotein translocase secy subunit | other |
| L13923 | Fibrillin | ECM |
| T91563 | cDNA clone 118372 similar to CD44 antigen, epithelial form precursor | signal transduction |
| J05017 | Aldose reductase | other |
| M55210 | (LAMB 2) gene Laminin B2 chain | ECM |
| M13755 | Interferon-induced 17 KD protein | other |
| U32114 | Caveolin-2 | signal transduction |
| X17097 | PSG9 | other |
| X52679 | Sphingomyelin phosphodiesterase | protein process. |
| Z48481 | Membrane-type matrix metalloproteinase 1 | protein process. |
| U24389 | Lysyl oxidase-like protein | cell ad./cell-cell comm. |
| M85289 | Heparan sulfate proteoglycan | cell ad./cell-cell comm. |
| D29992 | Placental protein 5 | other |
| Y00711 | L-lactate dehydrogenase H chain | other |
| R50499 | Fibrinogen beta chain precursor | cell ad./cell-cell comm. |
| U09278 | Fibroblast activation protein | signal transduction |
| H15811 | cDNA clone 159533 similar to Platelet membrane glycoprotein IIB precursor | cell ad./cell-cell comm. |
| X82494 | Fibulin-2 | ECM |
| H37925 | cDNA clone 190993 similar to Interferon-activatable protein 204 | other |
| J02685 | Plasminogen activator inhibitor-2 | protein process |
| U03106 | Wild-type p53 activated fragment-1, p21WAF1/CIP1 | cell-cycle |
| D13665 | Osteoblast specific factor 2 | cell ad./cell-cell comm. |
| T55741 | cDNA clone 73645 similar to Myosin light chain kinase | cell ad./cell-cell comm. |
| U18467 | Pregnancy-specific beta 1-glycoprotein 7 | other |
| X06700 | Pro-alpha1 (III) collagen | ECM |
| H56627 | cDNA clone 231424 similar to Glutathione S-transferase P | other |
| T41199 | cDNA clone 62328 similar to Laminin gamma-1 chain precursor | ECM |
| T59895 | cDNA clone 76290 similar to Ubiquitin carboxyl-terjminal hydrolase isozyme L1 | other |
| T68426 | CD81 antigen | cell ad./cell-cell comm. |
| X13810 | OTF-2 | transcription factor. |
| T50086 | cDNA clone 70213 similar to Alpha-1-antiproteinase F precursor | protein process. |

FIG. 10K

| | | |
|---|---|---|
| D28137 | Human mRNA for BST-2 | cell ad./cell-cell comm. |
| Z37976 | Latent TGF-beta binding protein | other |
| X02492 | Interferon-induced protein 6-16 precursor | other |
| T66960 | cDNA clone 66508 3' similar to Nuclear factor 1 clone PNF1/X | other |
| H88938 | Keratinocyte growth factor precursor | secr. gr. fact. |
| M29150 | Interleukin 6 | secr. gr. fact. |
| X05231 | Collagenase | protein process. |
| X68148 | p66shc | signal transduction |
| D31762 | KIAA0057 for ORF | cell-cycle |
| T61090 | cDNA clone 83635 similar to Endoglin precursor | signal transduction |
| T53889 | cDNA clone 78017 similar to Complement C1R component precursor | other |
| X58288 | hR-PTPu gene for protein tyrosine phosphatase | signal transduction |
| T51913 | cDNA clone 72466 similar to Alpha crystallin B chain | other |
| X17042 | Hematopoetic proteoglycan core protein | cell ad./cell-cell comm. |
| M55621 | N-acetylglucosaminyltransferase I | protein process. |
| H85111 | cDNA clone 220183 similar to EBNA-2 nuclear protein | transcription factor |
| X63613 | Pentaxin | other |
| M24594 | Interferon-induced 56 KD protein | other |
| R36467 | cDNA clone 136821 similar to Transforming growth factor beta 1 precursor | secr. gr. fact. |
| M87503 | Transcriptional regulator ISGF3 gamma subunit | transcription factor |
| X13097 | Tissue type plasminogen activator | cell ad./cell-cell comm. |
| X60201 | Brain-derived neurotrophic factor | other |
| M63509 | Human glutathione transferase M2 | other |
| M92642 | Alpha-1 type XVI collagen | ECM |
| M80469 | MHC class I HLA-J | other |

FIG. 10L

| ID | Description | Category |
|---|---|---|
| T60855 | cDNA clone 76721 similar to Calcineurin B subunit isoform 1 | signal transduction |
| X16707 | Fra-1 | transcription factor |
| H54425 | cDNA 203126 similar to Metallothionein-II | other |
| L04733 | Kinesin light chain | structural/cytoskeletal |
| R46493 | cDNA clone 36200 similar to Tissue factor precursor | ECM |
| M29696 | Interleukin-7 receptor alpha chain precursor | signal transduction |
| T97948 | cDNA clone 121916 similar to Calponin H2, smooth muscle | structural/cytoskeletal |
| R43953 | cDNA clone 33191 similar to Opioid binding protein | cell ad./cell-cell comm. |
| R16659 | cDNA clone 129622 similar to Tissue factor pathway inhibitor | cell ad./cell-cell comm. |
| U37019 | Smooth muscle cell calponin | structural/cytoskeletal |
| M96322 | Gravin | cell ad./cell-cell comm. |
| T78624 | cDNA clone 113518 similar to Carbonyl reductase | other |
| M60974 | GADD45 | cell-cycle |
| X60708 | pcHDP7 | protein process. |
| M62424 | Thrombin receptor precursor | signal transduction |
| R94513 | cDNA clone 197667 similar to STAT2 | signal transduction |
| V00523 | HLA-DR alpha | other |
| H65605 | cDNA clone 209780 similar to Prothrombin precursor | signal transduction |
| X76488 | Lysosomal acid lipase | protein process. |
| R12676 | cDNA clone 129303 similar to Complement factor H-like protein 1 precursor | other |
| X06985 | Heme oxygenase | metabolic enz. |
| R60908 | cDNA clone 42188 similar to protein-tyrosine kinase | signal transduction |
| U25779 | Human chromosome 17q21 mRNA clone 694:2 | other |
| X12496 | Erythrocyte membrane sialoglycoprotein beta | other |
| T71207 | cDNA clone 110162 similar to RAS-related C3 Botulinum toxin substrate 2 | signal transduction |

FIG. 10M

| Accession | Description | Category |
|---|---|---|
| R52961 | cDNA clone 40303 similar to Shc transforming protein 46.8 KD and 51.7 KD precursor | signal transduction |
| M97676 | Homeobox protein | transcription factor |
| R95874 | cDNA clone 199264 similar to LTR5 Retrovirus-related ENV polyprotein | other |
| T86469 | cDNA clone 114641 similar to Collagen alpha 3(VI) chain | ECM |
| R48243 | cDNA clone 153769 similar to RAS-related protein RHA1 | signal transduction |
| U19969 | Two-handed zinc finger protein ZEB | transcription factor |

Nominal copy number: 1-10 copies/cell

| Accession | Description | Category |
|---|---|---|
| R99935 | cDNA clone 201757 similar to DNA-directed RNA pol I largest subunit | transcription mach. |
| T64142 | cDNA clone 80145 similar to Proteolipid protein PPA1 | protein process. |
| H74007 | cDNA clone 232946 similar to Serine/threonine-protein kinase SGK | signal transduction |
| H47650 | PTS system, sucrose-spec. IIABC component | other |
| J04080 | Complement component C1r | other |
| D90226 | OSF-1 | secr. gr. fact. |
| X03348 | Human mRNA for beta-glucocorticoid receptor | signal transduction |
| R32804 | cDNA clone 135146 similar to Glucose transporter type 3 | other |
| M60618 | Nuclear autoantigen SP-100 | other |
| L13463 | Human helix-loop-helix basic phosphoprotein | other |
| M26683 | Human interferon gamma treatment inducible mRNA. | other |
| M63838 | Interferon-gamma induced protein | other |
| X73608 | Testican | cell ad./cell-cell comm. |
| M88338 | Serum protein MSE55 | other |
| T52698 | cDNA clone 67233 similar to Protein-tyrosine phosphatase 1B | protein process. |
| U16307 | Glioma pathogenesis-related protein | other |
| R35976 | cDNA clone 137079 similar to CD30 ligand | signal transduction |
| X16665 | HOX2H | transcription factor |
| R42244 | cDNA clone 30543 similar to Antigen peptide transporter 1 | protein process |
| U19718 | Human microfibril-associated glycoprotein | ECM |
| T85165 | cDNA clone 111345 similar to SRC substrate P80/85 proteins | signal transduction |
| R45687 | Cyclin G | cell-cycle |
| L22473 | Bax | cell-cycle |

Message quantities are expressed as nominal copy number per cell relative to hybridization intensities of known copy number spiked controls.
Abbreviations: secr. gr. fact., secreted growth factor; ad., adhesion; comm., communication; mach., machinery; enz., enzyme; pross., processing; ECM, extracellular matrix.

EXPRESSION MONITORING FOR GENE FUNCTION IDENTIFICATION

RELATED APPLICATION

This application is a divisional of U.S. application Ser. No. 09/086,285, filed May 29, 1998 now U.S. Pat. No. 6,303,301, which is a continuation-in-part of PCT application U.S. Ser. No. 98/01206 filed Jan. 12, 1998, which claims priority to provisional application No. 60/035,327 filed Jan. 13, 1997 (expired). All of the above applications are incorporated herein by reference.

BACKGROUND OF THE INVENTION

Many biological functions are accomplished by altering the expression of various genes through transcriptional (e.g. through control of initiation, provision of RNA precursors, RNA processing, etc.) and/or translational control. For example, fundamental biological processes such as cell cycle, cell differentiation and cell death, are often characterized by the variations in the expression levels of groups of genes.

Gene expression is also associated with pathogenesis. For example, the lack of sufficient expression of functional tumor suppressor genes and/or the over expression of oncogene/protooncogenes could lead to tumorgenesis (Marshall, *Cell*, 64: 313–326 (1991); Weinberg, Science, 254: 1138–1146 (1991), incorporated herein by reference for all purposes). Thus, changes in the expression levels of particular genes (e.g. oncogenes or tumor suppressors) serve as signposts for the presence and progression of various diseases.

The study of gene expression in the art has been generally concentrated on the regulatory regions of the gene of interest and on the relationships among a few genes. A number of transcriptional factors/DNA binding proteins have been identified and a limited number of regulatory pathways have been discovered. However, the expression of a particular gene is frequently regulated by the expression of a large number of other genes. The expression of those regulatory genes may also be under the control of additional genes. This complex regulatory relationship among genes constitutes a genetic network. The function and regulation of a particular gene can be best understood in the context of this genetic network. As the Human Genome Project and commercial genome research progress at a great rate, most, if not all, of the expressed genes will be partially sequenced in the near future. Understanding the functions and regulatory relationships among the large number of genes is becoming a difficult task with traditional tools. Therefore, there is a need in the art to develop a systematic approach to understand the complex regulatory relationships among large numbers of genes.

SUMMARY OF THE INVENTION

This invention provides methods, compositions, and apparatus for studying the complex regulatory relationships among genes. In some of its specific applications, this invention provides methods, compositions, and apparatus for detecting mutations of upstream regulatory genes by monitoring the expression of down-stream genes. In some embodiments, gene expression monitoring is used to determine certain functions of a gene by identifying its downstream regulated genes. Similar embodiments use gene expression to discern the effect of specific mutations of upstream genes. Gene expression is also used to identify upstream regulatory genes in some embodiments. By combining these approaches, this invention can be used to interrogate the genetic regulatory network and to construct a map indicating regulatory relationships.

Specifically, in one aspect of the invention, gene expression monitoring is used to decipher the complex regulatory relationship among genes. In such embodiments, the expression of more than 10 genes, preferably more than 100 genes, more preferably more than 1,000 genes and most preferably more than 5,000 genes are monitored in a large number of samples of cells. In some embodiments, each of the samples has an expression pattern different from that of other samples. In preferred applications a plurality of independent samples are assayed. The expression data can be analyzed to understand the complex relationships among genes. Ultimately, the expression data are analyzed to develop a map describing such complex relationships.

The invention provides methods to obtain biological samples representing a large number of independent states of gene expression. In some embodiments, antisense oligonucleotides or antisense genes are used to block the expression of specific genes. In other embodiments, homozygous, knock-out techniques are used to specifically suppress the expression of genes. In other embodiments transfection of regulatory genes is used to alter the expression profile of a cell. In some additional embodiments, antisense oligonucleotides of random sequence are introduced to cells to block the expression of genes.

In one such embodiment, expression data are analyzed to generate cluster maps indicating a correlation among genes. In some preferred embodiments, such cluster maps are then analyzed using statistical methods to generate a map consisting of regulatory pathways describing the complex relationship among the genes. Many statistical methods are suitable for building such maps. The LISREL method is particularly useful in such application. In some embodiments, the structure of the map is refined as more data become available. Thus, the map is dynamic and updated automatically as new data sets are entered.

Such a gene network map has a wide variety of applications, such as in the fields of diagnostics, drug discovery, gene therapy, and biological research. For example, an investigator interested in a particular gene may consult such a map to find putative upstream and downstream genes with statistical confidence. The investigator can then focus further research on those genes.

In another aspect of the invention, gene expression monitoring is used to detect potential malfunction of regulatory genes. In some embodiments, the expression of a subset of genes of interest in a diseased tissue is analyzed to obtain a diseased expression pattern. The subset contains at least one or more than 5, 10, 20, 25, 50, 75, 100, 150, 200, 250, 300, 400, 500, 750, 1,000, 1,250, 1500, 3000, 4550, or 6,000 genes of all the known genes. The expression of the same genes in a normal tissue can also be similarly analyzed to generate a normal gene expression pattern. Difference in the expression of genes indicates the abnormality of regulation in the diseased tissue. In some embodiments, a data filter is used to identify those genes whose expression is significantly altered. By using a data filter, only those genes whose expression is enhanced or reduced in the diseased tissue more than, e.g., 3, 5, or 10-fold are identified as altered.

Once the expression of a gene is found to be altered in the diseased tissue, the upstream regulatory gene of the altered gene is indicated as a candidate malfunctioning gene. In some embodiments, a upstream gene is identified as a candidate malfunctioning gene only if the expression of two or more of its down-stream genes is affected. The candidate malfunctioning gene is then sequenced to check whether a mutation is present, or the malfunction is due to epigenetic or nongenetic effectors. In some cases a mutation may not be present in the genome, and yet the product of the regulatory gene appears to be malfunctioning. For example, p53 can be functionally rather than genetically inactivated by binding to viral proteins, such as E1B and large T antigen. By assaying for the ability of a regulatory protein to activate or repress other gene's expression, the both genetic and phenotypic inactivation can be assessed.

In yet another aspect of the invention, the function of a particular mutation in a regulatory gene can be determined by gene expression monitoring. In some specific embodiments, the expression profiles of cells containing the specific mutation and control cells lacking the mutation are compared to determine whether the mutation affects the expression of down-stream genes. Similarly, the function of a particular gene may be determined. In such embodiments, the expression of a large number of genes is monitored in biological samples with the target gene expression to produce a control expression profile. The expression of the target gene is then suppressed to produce a target expression profile. By comparing the two expression profiles, one can identify potential regulated down-stream genes from affected genes.

In one specific embodiment, p53 activated and repressed genes are monitored to detect loss of wild-type p53 function. In another specific embodiment, gene expression monitoring is used to detect the in-cell function of p53.

According to yet another embodiment loss of function of a nucleic acid encoding a regulatory molecule in a test cell can be determined. A first nucleic acid molecule encoding a regulatory molecule is selected for analysis. A set of second nucleic acid molecules whose expression is induced or repressed by the regulatory molecule in normal cells is compiled or selected. A transcription indicator of a test cell is hybridized to a set of nucleic acid probes. The transcription indicator is selected from the group consisting of mRNA, cDNA and cRNA. Each member of the set of nucleic acid probes comprises a portion of a nucleic acid molecule which is a member of the set of second nucleic acid molecules which are induced or repressed by the selected regulatory molecule. The amount of transcription indicator which hybridizes to each of said set of nucleic acid probes is determined. A test cell is identified as having lost function of the regulatory molecule if (1) hybridization of the transcription indicator of the test cell to a probe which comprises a portion of a nucleic acid which is induced by the regulatory molecule is lower than hybridization using a transcription indicator from a normal cell, or (2) hybridization of the transcription indicator of the test cell to a probe which comprises a portion of a nucleic acid which is repressed by the regulatory molecule is higher than hybridization using a transcription indicator from a normal cell.

Monitoring of gene expression can be used to help elucidate gene function. For example, one can determine what other genes are coordinately expressed with a gene of interest when the gene of interest is genetically altered or subjected to a chemical which affects its expression. Conversely one can determine which upstream genes control expression of the gene of interest by knocking out putative upstream genes and monitoring expression of the gene. Of particular interest are those genes involved in basic biological processes, such as mitosis, mismatch repair, and apoptosis, those genes involved in development, and those genes involved in infections by viruses and other pathogens. Thus gene expression monitoring can be used to discern functions and relationships among genes, as well as to dissect signaling pathways and networks.

Pathological states can be characterized by patterns of gene expression. Thus diseased and matched normal tissues can be monitored and compared to devise a disease "fingerprint". This fingerprint can be used to diagnose other patients once established. Disease states include cancers, dysplasia, viral infections, parasite infections, bacterial infections, etc.

Gene expression monitoring can be used to establish developmental stages, for example, of a differentiating tissue, of an embryo, or of a fetus. A distinctive pattern of gene expression can be established for a particular stage by comparisons to closely and/or distantly related stages. Such patterns can be used for developmental staging of cells or tissues.

Potential chemotherapeutic agents can be screened or evaluated for their ability to alter a distinctive "fingerprint", for example, altering a "fingerprint" of a disease state to a "fingerprint" of a non-licensed state. Similarly agents can be screened for the ability to alter a differentiation state (fingerprint) of cells or tissues. Gene expression monitoring can be used for any stage of screening and development of therapeutic agents. It can be used for initial identification of lead compounds. It can be used for monitoring purification of compounds. It can be used for monitoring efficacy of modified forms of therapeutic agents or lead compounds. Expression monitoring is useful in any stage of research and development for discovering therapeutic agents.

DETAILED DESCRIPTION OF THE INVENTION

I. Definitions

Figure 1:
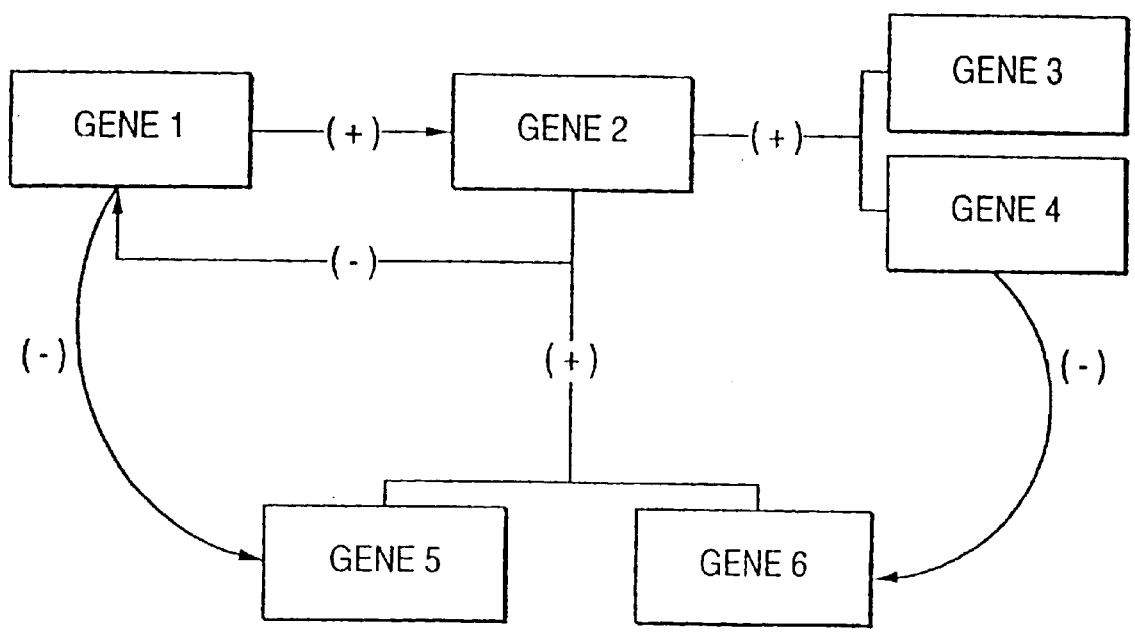
FIG. 1 shows a hypothetical genetic network.
Figure 2:
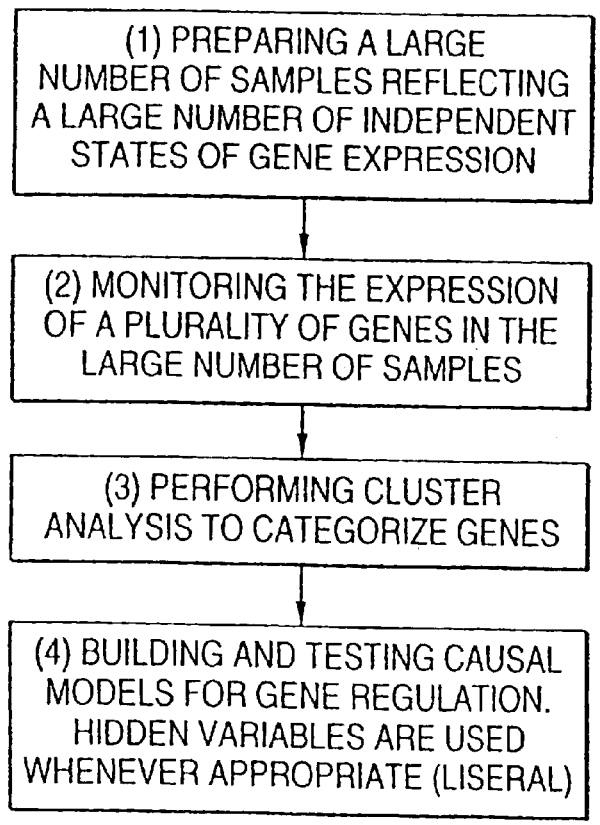
FIG. 2 shows a schematic of one embodiment for interrogating the genetic network.

II. Use of Gene Expression Monitoring for Genetic Network Mapping and Gene Function Identification III. Detecting the Regulation of Gene Expression
  a) cis-acting transcriptional control sequences, transcriptional factors and measurement of transcription rate
  b) different gene products from a single transcription unit
  c) Epigenetic mechanisms and long range control of genetic expression IV. Massive Parallel Gene Expression Monitoring
  (A) Providing a Nucleic Acid Sample
  (B) Hybridizing nucleic acids to high density array
  (C) Signal Detection V. Genetic Network and Interrogating the Genetic Network by Expression Monitoring
  (A) Artificial Cell Lines
  (B) Statistical Analysis VI. Identifying the Function of a Gene or a Mutation by Expression Monitoring
  Example 1. Identification of Function of a p53 Mutation VII. Mutation Detection by Gene Expression Monitoring
  Example 2. Detection of Heterozygous Functional Mutations in the p53 Gene I. Definitions Bind(s) Substantially "Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

Background

The terms "background" or "background signal intensity" refer to hybridization signals resulting from non-specific binding, or other interactions, between the labeled target nucleic acids and components of the oligonucleotide array (e.g., the oligonucleotide probes, control probes, the array substrate, etc.). Background signals may also be produced by intrinsic fluorescence of the array components themselves. A single background signal can be calculated for the entire array, or a different background signal may be calculated for each target nucleic acid. In a preferred embodiment, background is calculated as the average hybridization signal intensity for the lowest 5% to 10% of the probes in the array, or, where a different background signal is calculated for each target gene, for the lowest 5% to 10% of the probes for each gene. Of course, one of skill in the art will appreciate that where the probes to a particular gene hybridize well and thus appear to be specifically binding to a target sequence, they should not be used in a background signal calculation. Alternatively, background may be calculated as the average hybridization signal intensity produced by hybridization to probes that are not complementary to any sequence found in the sample (e.g. probes directed to nucleic acids of the opposite sense or to genes not found in the sample such as bacterial genes where the sample is mammalian nucleic acids). Background can also be calculated as the average signal intensity produced by regions of the array that lack any probes at all.

Cis-acting

The term "cis-acting" is used here to refer to the regulation of gene expression by a DNA subsequence in the same DNA molecule as the target gene. Cis-acting can be exerted either by the binding of trans-acting transcriptional factors or by long range control.

Complexity

The term "complexity" is used here according to standard meaning of this term as established by Britten et al. *Methods of Enzymol.* 29:363 (1974). See, also *Cantor and Schimmel Biophysical Chemistry: Part III* at 1228–1230 for further explanation of nucleic acid complexity.

Hybridizing Specifically to

The phrase "hybridizing specifically to" refers to the binding, duplexing, or hybridizing of a molecule substantially to or only to a particular nucleotide sequence or sequences under stringent conditions when that sequence is present in a complex mixture (e.g., total cellular) DNA or RNA.

Introns noncoding DNA sequences which separate neighboring coding regions. During gene transcription, introns, like exons, are transcribed into RNA but are subsequently removed by RNA splicing.

Massive Parallel Screening

The phrase "massively parallel screening" refers to the simultaneous screening of at least about 100, preferably about 1000, more preferably about 10,000 and most preferably about 1,000,000 different nucleic acid hybridizations.

Mismatch Control

The term "mismatch control" or "mismatch probe" refer to a probe whose sequence is deliberately selected not to be perfectly complementary to a particular target sequence. For each mismatch (MM) control in a high-density array there typically exists a corresponding perfect match (PM) probe that is perfectly complementary to the same particular target sequence. The mismatch may comprise one or more bases. While the mismatch(es) may be located anywhere in the mismatch probe, terminal mismatches are less desirable as a terminal mismatch is less likely to prevent hybridization of the target sequence. In a particularly preferred embodiment, the mismatch is located at or near the center of the probe such that the mismatch is most likely to destabilize the duplex with the target sequence under the test hybridization conditions.

mRNA or Transcript

The term "mRNA" refers to transcripts of a gene. Transcripts are RNA including, for example, mature messenger RNA ready for translation, products of various stages of transcript processing. Transcript processing may include splicing, editing and degradation.

Nucleic Acid

The terms "nucleic acid" or "nucleic acid molecule" refer to a deoxyribonucleotide or ribonucleotide polymer in either single-or double-stranded form, and unless otherwise limited, would encompass analogs of natural nucleotide that can function in a similar manner as naturally occurring nucleotide. An oligo-nucleotide is a single-stranded nucleic acid of 2 to n bases, where n may be greater than 500 to 1000. Nucleic acids may be cloned or synthesized using any technique known in the art. They may also include non-naturally occurring nucleotide analogs, such as those which are modified to improve hybridization and peptide nucleic acids.

Nucleic Acid Encoding a Regulatory Molecule

The regulatory molecule may be DNA, RNA or protein. Thus for example DNA sites which bind protein or other nucleic acid molecules are included within the class of regulatory molecules encoded by a nucleic acid.

Perfect Match Probe

The term "perfect match probe" refers to a probe that has a sequence that is perfectly complementary to a particular target sequence. The test probe is typically perfectly complementary to a portion (subsequence) of the target sequence. The perfect match (PM) probe can be a "test probe", a "normalization control" probe, an expression level control probe and the like. A perfect match control or perfect match probe is, however, distinguished from a "mismatch control" or "mismatch probe."

Probe

As used herein a "probe" is defined as a nucleic acid, capable of binding to a target nucleic acid of complementary sequence through one or more types of chemical bonds, usually through complementary base pairing, usually through hydrogen bond formation. As used herein, a probe may include natural (i.e. A, G, U, C, or T) or modified bases (7-deazaguanosine, inosine, etc.). In addition, the bases in probes may be joined by a linkage other than a phosphodiester bond, so long as it does not interfere with hybridization. Thus, probes may be peptide nucleic acids in which the constituent bases are joined by peptide bonds rather than phosphodiester linkages.

Target Nucleic Acid

The term "target nucleic acid" refers to a nucleic acid (often derived from a biological sample), to which the probe is designed to specifically hybridize. It is either the presence or absence of the target nucleic acid that is to be detected, or the amount of the target nucleic acid that is to be quantified. The target nucleic acid has a sequence that is complementary to the nucleic acid sequence of the corresponding probe directed to the target. The term target nucleic acid may refer to the specific subsequence of a larger nucleic acid to which the probe is directed or to the overall sequence (e.g., gene or mRNA) whose expression level it is desired to detect. The difference in usage will be apparent from context.

Trans-acting

The term "trans-acting" refers to regulation of gene expression by a product that is encoded by a gene at a remote location, usually as a result of binding to a cis-element.

Stringent Conditions

The term "stringent conditions" refers to conditions under which a probe will hybridize to its target subsequence, but with only insubstantial hybridization to other sequences or to other sequences such that the difference may be identified. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH.

Subsequence

"Subsequence" refers to a sequence of nucleic acids that comprise a part of a longer sequence of nucleic acids.

Thermal Melting Point (Tm)

The Tm is the temperature, under defined ionic strength, pH, and nucleic acid concentration, at which 50% of the probes complementary to the target sequence hybridize to the target sequence at equilibrium. As the target sequences are generally present in excess, at Tm, 50% of the probes are occupied at equilibrium). Typically, stringent conditions will be those in which the salt concentration is at least about 0.01 to 1.0 M Na ion concentration (or other salts) at pH 7.0 to 8.3 and the temperature is at least about 30 C. for short probes (e.g., 10 to 50 nucleotide). Stringent conditions may also be achieved with the addition of destabilizing agents such as formamide.

Quantifying

The term "quantifying" when used in the context of quantifying transcription levels of a gene can refer to absolute or to relative quantification. Absolute quantification may be accomplished by inclusion of known concentration(s) of one or more target nucleic acids (e.g. control nucleic acids such as Bio B or with known amounts the target nucleic acids themselves) and referencing the hybridization intensity of unknowns with the known target nucleic acids (e.g. through generation of a standard curve). Alternatively, relative quantification can be accomplished by comparison of hybridization signals between two or more genes, or between two or more treatments to quantify the changes in hybridization intensity and, by implication, transcription level.

Sequence Identity

The "percentage of sequence identity" or "sequence identity" is determined by comparing two optimally aligned sequences or subsequences over a comparison window or span, wherein the portion of the polynucleotide sequence in the comparison window may optionally comprise additions or deletions (i.e., gaps) as compared to the reference sequence (which does not comprise additions or deletions) for optimal alignment of the two sequences. The percentage is calculated by determining the number of positions at which the identical subunit (e.g. nucleic acid base or amino acid residue) occurs in both sequences to yield the number of matched positions, dividing the number of matched positions by the total number of positions in the window of comparison and multiplying the result by 100 to yield the percentage of sequence identity. Percentage sequence identity when calculated using the programs GAP or BESTFIT (see below) is calculated using default gap weights.

Methods of alignment of sequences for comparison are well known in the art. Optimal alignment of sequences for comparison may be conducted by the local homology algorithm of Smith and Waterman, *Adv. Appl. Math.* 2: 482 (1981), by the homology alignment algorithm of Needleman and Wunsch *J. Mol. Biol.* 48: 443 (1970), by the search for similarity method of Pearson and Lipman, *Proc. Natl. Acad. Sci. USA* 85: 2444 (1988), by computerized implementations of these algorithms (including, but not limited to CLUSTAL in the PC/Gene program by Intelligenetics, Moutain View, Calif., GAP, BESTFIT, FASTA, and TFASTA in the Wisconsin Genetics Software Package, Genetics Computer Group (GCG), 575 Science Dr., Madison, Wis., USA), or by inspection. In particular, methods for aligning sequences using the CLUSTAL program are well described by Higgins and Sharp in *Gene,* 73: 237–244 (1988) and in *CABIOS* 5: 151–153 (1989)).

Up-stream or Down-stream Gene

If the expression of a first gene is regulated by a second gene, the second gene is called an "up-stream gene" for the first gene and the first gene is the "down-stream" gene of the second gene. The regulation of the first gene by second gene could be through trans-activation. For example, the first gene encodes a transcriptional factor that controls the expression of the second gene. The regulation can also be exerted by cis-acting. For example, the first gene is in the proximity of the second gene and exerts a positional effect on the expression of the second gene. In this case, the first gene does not have to be expressed in order to have an influence on the second gene.

II. Use of Gene Expression Monitoring for Genetic Network Mapping and Gene Function Identification This invention provides methods, compositions and apparatus for interrogating the genetic network and for studying normal and abnormal functions for specific genes. The methods involve quantifying the level of expression of a large number of genes. In some preferred embodiments, a high density oligonucleotide array is used to hybridize with a target nucleic acid sample to detect the expression level of a large number of genes, preferably more than 10, more preferably more than 100, and most preferably more than 1000 genes.

A variety of nucleic acid samples are prepared according to the methods of the invention to represent many states of the genetic network. By comparing the expression levels of those samples, regulatory relationships among genes can be determined with a certain statistical confidence. A dynamic map can be constructed based upon expression data.

Such a genetic network map is extremely useful for drug discovery. For example, if a gene of interest is found to be associated with a particular disease, a list of potential up-stream regulatory genes can be found using such a genetic network map. Research efforts can then be concentrated on the potential up-stream genes as drug targets. Similarly, if a gene mutation causes a disease, it may affect genes that are both related and unrelated to the pathogenesis of the disease. The relationships can be explored to find the pathogenic genes. In such embodiments, the association between a disease state and the expression of a large number of genes is determined, and the genes whose expression is altered in the diseased tissue are identified. The up-stream genes that regulate the altered genes are indicated as functionally altered or potentially mutated.

In general, genetic regulatory relationships can be explored to detect potential mutations once a target gene's down-stream regulated genes are identified. In one embodiment of the invention, the expression of several down-stream positively regulated genes is monitored using a high density oligonucleotide array. Diminished expression of those positively regulated genes indicates a possible malfunction of the target gene. Such malfunction may indicate the presence of a potential mutation in the target gene. Other mutation detection methods, such as the tiling methods, can then be used to confirm and to detect the nature of the mutation. Many sets of such down-stream positively regulated genes, each set of genes being regulated by a target gene, can be monitored simultaneously. This simultaneous detection of mutations in many genes is an major improvement over prior art methods. It will be apparent to those skilled in the art that negatively regulated down-stream genes can also be used in a similar manner.

Similarly, in some embodiments, the regulatory function of a particular gene can be identified by monitoring a large number of genes. In one particularly preferred embodiment, the expression of a gene of interest is suppressed by applying antisense oligonucleotides. The expression of a large number of genes are monitored to provide an expression pattern. The expression of the gene of interest is then restored and the expression of a large number of genes are similarly monitored to provide another expression pattern. By comparing the expression patterns, the regulatory function of the gene of interest can be deduced.

III. Detecting the Regulation of Gene Expression

Activity of a gene is reflected by the activity of its product(s): the proteins or other molecules encoded by the gene. Those product molecules perform biological functions. Directly measuring the activity of a gene product is, however, often difficult for certain genes. Instead, the immunological activities or the amount of the final product(s) or its peptide processing intermediates are determined as a measurement of the gene activity. More frequently, the amount or activity of intermediates, such as transcripts, RNA processing intermediates, or mature mRNAs are detected as a measurement of gene activity.

In many cases, the form and function of the final product(s) of a gene is unknown. In those cases, the activity of a gene is measured conveniently by the amount or activity of transcript(s), RNA processing intermediate(s), mature mRNA(s) or its protein product(s) or functional activity of its protein product(s).

Any methods that measure the activity of a gene are useful for at least some embodiments of this invention. For example, traditional Northern blotting and hybridization, nuclease protection, RT-PCR and differential display have been used for detecting gene activity. Those methods are useful for some embodiments of the invention. However, this invention is most useful in conjunction with methods for detecting the expression of a large number of genes.

High density arrays are particularly useful for monitoring the expression control at the transcriptional, RNA processing and degradation level. The fabrication and application of high density arrays in gene expression monitoring have been disclosed previously in, for example, WO 97/10365, WO 92/10588, U.S. application Ser. No. 08/772,376 filed Dec. 23, 1996; Ser. No. 08/529,115 filed on Sep. 15, 1995; Ser. No. 08/168,904 filed Dec. 15, 1993; Ser. No. 07/624,114 filed on Dec. 6, 1990, Ser. No. 07/362,901 filed Jun. 7, 1990, all incorporated herein for all purposed by reference. In some embodiment using high density arrays, high density oligonucleotide arrays are synthesized using methods such as the Very Large Scale Immobilized Polymer Synthesis (VLSIPS) disclosed in U.S. Pat. No. 5,445,934 incorporated herein for all purposes by reference. Each oligonucleotide occupies a known location on a substrate. A nucleic acid target sample is hybridized with a high density array of oligonucleotides and then the amount of target nucleic acids hybridized to each probe in the array is quantified. One preferred quantifying method is to use confocal microscope and fluorescent labels. The GeneChip® system (Affymetrix, Santa Clara, Calif.) is particularly suitable for quantifying the hybridization; however, it will be apparent to those of skill in the art that any similar systems or other effectively equivalent detection methods can also be used.

High density arrays are suitable for quantifying a small variations in expression levels of a gene in the presence of a large population of heterogeneous nucleic acids. Such high density arrays can be fabricated either by de novo synthesis on a substrate or by spotting or transporting nucleic acid sequences onto specific locations of substrate. Nucleic acids are purified and/or isolated from biological materials, such as a bacterial plasmid containing a cloned segment of sequence of interest. Suitable nucleic acids are also produced by amplification of templates. As a nonlimiting illustration, polymerase chain reaction, and/or in vitro transcription, are suitable nucleic acid amplification methods.

Synthesized oligonucleotide arrays are particularly preferred for this invention. Oligonucleotide arrays have numerous advantages, as opposed to other methods, such as efficiency of production, reduced intra- and inter array variability, increased information content and high signal-to-noise ratio.

Preferred high density arrays for gene function identification and genetic network mapping comprise greater than about 100, preferably greater than about 1000, more preferably greater than about 16,000 and most preferably greater than 65,000 or 250,000 or even greater than about 1,000,000 different oligonucleotide probes, preferably in less than 1 $cm^2$ of surface area. The oligonucleotide probes range from about 5 to about 50 or about 500 nucleotides, more preferably from about 10 to about 40 nucleotide and most preferably from about 15 to about 40 nucleotides in length.

One of skill in the art would appreciate that in order to interrogate the genetic network, it is desirable to measure the control of transcription. Because all the cell nuclei of an organism generally carry the same genes, the difference in the protein products in different cell types is generally the result of selective gene expression. It is well known in the art that the first level of regulation is at the level of transcription, i.e., by varying the frequency with which a gene is transcribed into nascent pre-mRNA by a RNA polymerase. The regulation of transcription is one of the most important steps in the control of gene expression because transcription constitutes the input of the mRNA pool. It is generally known in the art that transcriptional regulation can be achieved through various means. As non-limiting examples, transcription can be controlled by a) cis-acting transcriptional control sequences and transcriptional factors; b) different gene products from a single transcription unit and c) epigenetic mechanisms; and d) long range control of genetic expression by chromatin structure. The current invention provides methods for detecting the transcriptional regulation of individual genes at all of these levels of control.

a) Cis-acting Transcriptional Control Sequences, Transcriptional Factors and Measurement of Transcription Rate One level of transcriptional control is through the binding of transcriptional factors to the cis-acting transcriptional control sequences. A human gene often employs several cis-acting sequences. Promoters are a class of cis-acting elements usually located immediately up-stream (often within 200 bp) of the transcriptional start sites. Promoters (TATA box, CCAAT Box, GC box, etc.) are often recognized by ubiquitous transcriptional factors. In addition, promoters may be involved in the control of tissue-specific expression through the binding of tissue specific transcriptional factors. Another class of cis-acting elements are the response elements (REs). Those elements are typically found in genes whose expression is responsive to the presence of signaling molecules such as growth factors, hormones, and secondary messengers. Such elements include, but not limited to, cAMP REs, retinoic acid REs, growth factor REs, glucocorticoid REs. Enhancers and repressors are yet another class of the cis-acting elements. Those elements have a positive or negative effect on transcription and their functions are generally independent of their orientation in the gene.

Transcriptional factors are proteins that recognize and bind cis-acting trancriptional elements. Often, but not always, those factors contain two domains: a DNA-binding domain and an activation domain. The DNA-binding domain typically contains the leucine zipper motif, the helix-loop-helix motif, helix-turn-helix motif, and/or the zinc finger motif. Transcriptional factors are encoded by their own genes. Therefore, the expression level of transcriptional factors may affect the expression of other genes. Those trans-acting factors are integral part of the genetic network. In some embodiments of the invention, the expression of transcriptional factors is monitored by the use of a high density array. In some other embodiments, the expression of transcriptional factors are monitored at the protein level by the use of two dimensional gel electrophoresis, mass-spectrometry or immunological methods.

In some preferred embodiments, direct measurement, such as the nuclear run-on assay, of transcriptional rate is employed. In such embodiments, nuclei are isolated from cells of interest. Isolated nuclei are incubated with labeled nucleotides for a period of time. Transcripts are then hybridized with probes. In some preferred embodiments, transcripts are quantified with high density nucleic acid array.

b) Different Gene Products from a Single Transcription Unit

A transcriptional unit is a continuous segment of DNA that is transcribed into RNA. For example, bacteria can continuously transcribe several contiguous genes to make polycistronic mRNAs. The contiguous genes are from the same transcriptional unit. It is well known in the art that higher organisms also use several mechanisms to make a variety of different gene products from a single transcriptional unit.

Many genes are known to have several alternative promoters, the use of each promoter resulting one particular transcript. The use of alternative promoters is frequently employed to regulate tissue specific gene expression. For example, human dystrophin gene has at least seven promoters. The most 5' upstream promoter is used to transcribe a brain specific transcript; a promoter 100 kb down-stream from the first promoter is used to transcribe a muscle specific transcript and a promoter 100 kb downstream of the second promoter is used to transcribe Purkinje cell specific transcript. The use of alternative promoters is part of the gene network control mechanism. In several embodiments of the invention, the use of alternative promoters can be monitored and mapped to resolve its regulatory relationship among genes. In one preferred embodiment, a high density oligonucleotide array is used to monitor the use of specific promoters by measuring the amount of transcripts resulting from each of the alternative promoters. In such embodiments, probes are designed to be specific for each of the exons that are alternatively used. A high density oligonucleotide array is particularly useful for this purpose because of the flexibility of probe design. However, one of ordinary skill in the art would appreciate that other methods, such as DNA arrays, RT-PCR, differential display, optical oligonucleotide sensors, can also be used to monitor the alternative use of promoters.

Similarly, alternative splicing and polyadenylation are also important mechanisms for regulating gene activity, frequently in a tissue specific manner. In eukaryotes, nascent pre-mRNAs are generally not translated into proteins. Rather, they are processed in several ways to generate mature mRNAs. RNA splicing is the most common method of RNA processing. Nascent pre-mRNAs are cut and pasted by specialized apparatus called splicesomes. Some non-coding regions transcribed from the intron regions are excised. Exons are linked to form a contiguous coding region ready for translation. In some splicing reactions, a single type of nascent pre-mRNAs are used to generate multiple types of mature RNA by a process called alternative splicing in which exons are alternatively used to form different mature mRNAs which code for different proteins. For example, the human Calcitonin gene (CALC) is spliced as calcitonin, a circulating $Ca^{2+}$ homeostatic hormone, in the thyroid; and as calcitonin gene-related peptide (CGRP), a neuromodulatory and trophic factor, in the hypothalamus (See, Hodges and Bernstein, 1994, Adv. Genet., 31, 207–281). This diversity of gene product is achieved by a combination of alternative splicing and alternative adenylation. Regulation of the alternative splicing and adenylation is a part of the genetic network. In some embodiments of the invention, alternative splicing are monitored. Many methods are suitable for detecting alternative splicing and adenylation. High density oligonucleotide arrays are particularly suitable for this purpose because of their design flexibility. Oligonucleotide probes against specific sequence diversity can be readily synthesized and used to detect the level of each of the sequences produced by alternative splicing and adenylation.

RNA editing is another form of post-transcriptional processing. For example, certain genes, such as the Wilm's tumor susceptibility gene (WTI), apolipoprotein (APOB) gene, and glutamate receptor gene undergo C->U or U->C substitution editing events (See, Scott, 1995, Cell, 81, 833–836). In the liver, the human APOB gene encodes a 4536 amino acid product. In the intestine, however, the same gene encodes a 2152 amino acid product. The smaller product is due to the addition of a stop codon during RNA editing. High density oligonucleotide arrays are particularly suitable for detecting RNA editing events. Because single base mismatches can be readily identified, oligonucleotide probes against each of potential RNA editing products are fabricated on a single substrate to detect the level of those products by specific hybridization.

c) Epigenetic Mechanisms and Long Range Control of Genetic Expression.

Even though majority of genes are expressed whether they are inherited from the mother or the father, the expression of some autosomal genes are affected by their origin. For example, the paternal allele of the Insulin like growth factor-II gene is expressed; while the maternal allele of the H-19 tumor suppressor RNA is expressed. This phenomenon is called genomic imprinting. In some embodiments of the invention, genomic imprinting can be monitored by measuring the level of transcripts of specific sequence.

Long range control of gene expression provides additional means for one gene to interact with another in expression. Competition for enhancers or silencers, position effects, chromatin domains and X-inactivation are mechanisms for a region of DNA or a gene to exert its control over the expression of other genes without expressing itself Long range control of gene expression may increase the complexity of analyzing correlated gene expression data. For example, expression of certain genes may be correlated because of their proximity, not because they are under the control of the expressed product of a common gene. Knowledge regarding the position of genes is useful in analyzing such data. In some embodiments, a hidden variable (i.e., a variable that is not measurable by using expression monitoring) may be introduced to represent the long range control in data analysis. Long range control effects can be inferred by a consistent positional effect, i e., a correlation between expression and proximity of genes. Direct measurement of long range control over gene expression can be carried out by combining gene expression monitoring and traditional methods for identifying such control. Traditional methods are described in, for example, Strachan and Read, Human Molecular Genetics, 1996, incorporated herein by reference for all purposes.

The current invention is based upon the regulatory relationships among genes. It is well known in the art that gene expression is regulated at transcription, RNA processing, RNA degradation, translation, and protein processing levels. Some of the specific preferred embodiments of the invention monitor expression control at the transcription, RNA processing and degradation level. Those embodiments are described in detail to illustrate the methods of the invention. It would be apparent to those of ordinary skill in the art that monitoring translation and protein processing can be similarly used for the current invention. In some embodiments, antibodies are used to detect the amount of protein products using procedures such as Western blotting and immunocytochemistry. Other immunological methods can also be used. Traditional polyclonal or monoclonal antibodies are useful. Genetic engineering methods, such as the phage display technology described, for example, in Strachan and Read, Human Molecular Genetics, 1996, incorporated previously for all purposes by reference, are particularly preferred in some embodiments to obtain a large number of antibodies for monitoring the expression of a large number of genes.

IV. Massive Parallel Gene Expression Monitoring

One preferred method for massive parallel gene expression monitoring is based upon high density nucleic acid arrays. Nucleic acid array methods for monitoring gene expression are disclosed and discussed in detail in PCT Application WO 092.10588 (published on Jun. 25, 1992), all incorporated herein by reference for all purposes.

Generally those methods of monitoring gene expression involve (a) providing a pool of target nucleic acids comprising RNA transcript(s) of one or more target gene(s), or nucleic acids derived from the RNA transcript(s); (b) hybridizing the nucleic acid sample to a high density array of probes and (c) detecting the hybridized nucleic acids and calculating a relative and/or absolute expression (transcription, RNA processing or degradation) level.

(A). Providing a Nucleic Acid Sample

One of skill in the art will appreciate that it is desirable to have nucleic samples containing target nucleic acid sequences that reflect the transcripts of interest. Therefore, suitable nucleic acid samples may contain transcripts of interest. Suitable nucleic acid samples, however, may contain nucleic acids derived from the transcripts of interest. As used herein, a nucleic acid derived from a transcript refers to a nucleic acid for whose synthesis the mRNA transcript or a subsequence thereof has ultimately served as a template. Thus, a cDNA reverse transcribed from a transcript, an RNA transcribed from that cDNA, a DNA amplified from the cDNA, an RNA transcribed from the amplified DNA, etc., are all derived from the transcript and detection of such derived products is indicative of the presence and/or abundance of the original transcript in a sample. Thus, suitable samples include, but are not limited to, transcripts of the gene or genes, cDNA reverse transcribed from the transcript, cRNA transcribed from the cDNA, DNA amplified from the genes, RNA transcribed from amplified DNA, and the like. Transcripts, as used herein, may include, but not limited to pre-mRNA nascent transcript(s), transcript processing intermediates, mature mRNA(s) and degradation products. It is not necessary to monitor all types of transcripts to practice this invention. For example, one may choose to practice the invention to measure the mature mRNA levels only.

In one embodiment, such sample is a homogenate of cells or tissues or other biological samples. Preferably, such sample is a total RNA preparation of a biological sample. More preferably in some embodiments, such a nucleic acid sample is the total mRNA isolated from a biological sample. Those of skill in the art will appreciate that the total mRNA prepared with most methods includes not only the mature mRNA, but also the RNA processing intermediates and nascent pre-mRNA transcripts. For example, total mRNA purified with a poly (dT) column contains RNA molecules with poly (A) tails. Those polyA$^+$ RNA molecules could be mature mRNA, RNA processing intermediates, nascent transcripts or degradation intermediates.

Biological samples may be of any biological tissue or fluid or cells from any organism. Frequently the sample will be a "clinical sample" which is a sample derived from a patient. Clinical samples provide a rich source of information regarding the various states of genetic network or gene expression. Some embodiments of the invention are employed to detect mutations and to identify the phenotype of mutations. Such embodiments have extensive applications in clinical diagnostics and clinical studies. Typical clinical samples include, but are not limited to, sputum, blood, blood cells (e.g., white cells), tissue or fine needle biopsy samples, urine, peritoneal fluid, and pleural fluid, or cells therefrom. Biological samples may also include sections of tissues, such as frozen sections or formalin fixed sections taken for histological purposes.

Another typical source of biological samples are cell cultures where gene expression states can be manipulated to explore the relationship among genes. In one aspect of the invention, methods are provided to generate biological samples reflecting a wide variety of states of the genetic network.

One of skill in the art would appreciate that it is desirable to inhibit or destroy RNase present in homogenates before homogenates can be used for hybridization. Methods of inhibiting or destroying nucleases are well known in the art. In some preferred embodiments, cells or tissues are homogenized in the presence of chaotropic agents to inhibit nuclease. In some other embodiments, RNase is inhibited or destroyed by heat treatment followed by proteinase treatment.

Methods of isolating total mRNA are also well known to those of skill in the art. For example, methods of isolation and purification of nucleic acids are described in detail in Chapter 3 of *Laboratory Techniques in Biochemistry and Molecular Biology: Hybridization With Nucleic Acid Probes, Part I. Theory and Nucleic Acid Preparation*, P. Tijssen, ed. Elsevier, N.Y. (1993) and Chapter 3 of *Laboratory Techniques in Biochemistry and Molecular Biology: Hybridization With Nucleic Acid Probes, Part I. Theory and Nucleic Acid Preparation*, P. Tijssen, ed. Elsevier, N.Y. (1993)).

In a preferred embodiment, the total RNA is isolated from a given sample using, for example, an acid guanidinium-phenol-chloroform extraction method and polyA$^+$ mRNA is isolated by oligo(dT) column chromatography or by using (dT) on magnetic beads (see, e.g., Sambrook et al., *Molecular Cloning: A Laboratory Manual* (2nd ed.), Vols. 1–3, Cold Spring Harbor Laboratory, (1989), or *Current Protocols in Molecular Biology*, F. Ausubel et al., ed. Greene Publishing and Wiley-Interscience, New York (1987)).

Frequently, it is desirable to amplify the nucleic acid sample prior to hybridization. One of skill in the art will appreciate that whatever amplification method is used, if a quantitative result is desired, care must be taken to use a method that maintains or controls for the relative frequencies of the amplified nucleic acids to achieve quantitative amplification.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The high density array may then include probes specific to the internal standard for quantification of the amplified nucleic acid.

One preferred internal standard is a synthetic AW106 cRNA. The AW106 cRNA is combined with RNA isolated from the sample according to standard techniques known to those of skilled in the art. The RNA is then reverse transcribed using a reverse transcriptase to provide copy DNA. The cDNA sequences are then amplified (e.g., by PCR) using labeled primers. The amplification products are separated, typically by electrophoresis, and the amount of radioactivity (proportional to the amount of amplified product) is determined. The amount of mRNA in the sample is then calculated by comparison with the signal produced by the known AW106 RNA standard. Detailed protocols for quantitative PCR are provided in *PCR Protocols, A Guide to Methods and Applications,* Innis et al., Academic Press, Inc. N.Y., (1990).

Other suitable amplification methods include, but are not limited to polymerase chain reaction (PCR) (Innis, et al., *PCR Protocols. A guide to Methods and Application*. Academic Press, Inc. San Diego, (1990)), ligase chain reaction (LCR) (see Wu and Wallace, *Genomics,* 4: 560 (1989), Landegren, et al., *Science,* 241: 1077 (1988) and Barringer, et al., *Gene,* 89: 117 (1990), transcription amplification (Kwoh, et al., *Proc. Natl. Acad. Sci. USA,* 86: 1173 (1989)), and self-sustained sequence replication (Guatelli, et al., *Proc. Nat. Acad. Sci. USA,* 87: 1874 (1990)).

Cell lysates or tissue homogenates often contain a number of inhibitors of polymerase activity. Therefore, RT-PCR typically incorporates preliminary steps to isolate total RNA or mRNA for subsequent use as an amplification template. A one-tube mRNA capture method may be used to prepare poly(A)$^+$RNA samples suitable for immediate RT-PCR in the same tube (Boehringer Mannheim). The captured mRNA can be directly subjected to RT-PCR by adding a reverse transcription mix and, subsequently, a PCR mix.

In a particularly preferred embodiment, the sample mRNA is reverse transcribed with a reverse transcriptase and a primer consisting of oligo(dT) and a sequence encoding the phage T7 promoter to provide single stranded DNA template. The second DNA strand is polymerized using a DNA polymerase. After synthesis of double-stranded cDNA, T7 RNA polymerase is added and RNA is transcribed from the cDNA template. Successive rounds of transcription from each single cDNA template results in amplified RNA. Methods of in vitro polymerization are well known to those of skill in the art (see, e.g., Sambrook, supra.) and this particular method is described in detail by Van Gelder, et al., *Proc. Natl. Acad. Sci. USA,* 87: 1663–1667 (1990) who demonstrate that in vitro amplification according to this method preserves the relative frequencies of the various RNA transripts. Moreover, Eberwine et al. *Proc. Natl. Acad. Sci. USA,* 89: 3010–3014 provide a protocol that uses two rounds of amplification via in vitro transcription to achieve greater than $10^6$ fold amplification of the original starting material, thereby permitting expression monitoring even where biological samples are limited.

It will be appreciated by one of skill in the art that the direct transcription method described above provides an antisense (aRNA) pool. Where antisense RNA is used as the target nucleic acid, the oligonucleotide probes provided in the array are chosen to be complementary to subsequences of the antisense nucleic acids. Conversely, where the target nucleic acid pool is a pool of sense nucleic acids, the oligonucleotide probes are selected to be complementary to subsequences of the sense nucleic acids. Finally, where the nucleic acid pool is double stranded, the probes may be of either sense as the target nucleic acids include both sense and antisense strands.

The protocols cited above include methods of generating pools of either sense or antisense nucleic acids. Indeed, one approach can be used to generate either sense or antisense nucleic acids as desired. For example, the cDNA can be directionally cloned into a vector (e.g., Stratagene's p Bluscript II KS (+) phagemid) such that it is flanked by the T3 and T7 promoters. In vitro transcription with the T3 polymerase will produce RNA of one sense (the sense depending on the orientation of the insert), while in vitro transcription with the T7 polymerase will produce RNA having the opposite sense. Other suitable cloning systems include phage lambda vectors designed for Cre-loxP plasmid subdloning (see e.g., Palazzolo et al., *Gene,* 88: 25–36 (1990)).

(B) Hybridizing nucleic acids to high density arrays

1. Probe Design

One of skill in the art will appreciate that an enormous number of array designs are suitable for the practice of this invention. The high density array will typically include a number of probes that specifically hybridize to the sequences of interest. In addition, in a preferred embodiment, the array will include one or more control probes.

The high density array chip includes "test probes." Test probes could be oligonucleotides that range from about 5 to about 45 or 5 to about 500 nucleotides, more preferably from about 10 to about 40 nucleotides and most preferably from about 15 to about 40 nucleotides in length. In other particularly preferred embodiments the probes are 20 or 25 nucleotides in length. In another preferred embodiments, test probes are double or single strand DNA sequences. DNA sequences are isolated or cloned from nature sources or amplified from nature sources using nature nucleic acid as templates. These probes have sequences complementary to particular subsequences of the genes whose expression they are designed to detect. Thus, the test probes are capable of specifically hybridizing to the target nucleic acid they are to detect.

In addition to test probes that bind the target nucleic acid(s) of interest, the high density array can contain a number of control probes. The control probes fall into three categories referred to herein as 1) normalization controls; 2) expression level controls; and 3) mismatch controls.

Normalization controls are oligonucleotide or other nucleic acid probes that are complementary to labeled reference oligonucleotides or other nucleic acid sequences that are added to the nucleic acid sample. The signals obtained from the normalization controls after hybridization provide a control for variations in hybridization conditions, label intensity, "reading" efficiency and other factors that may cause the signal of a perfect hybridization to vary between arrays. In a preferred embodiment, signals (e.g., fluorescence intensity) read from all other probes in the array are divided by the signal (e.g., fluorescence intensity) from the control probes thereby normalizing the measurements.

Virtually any probe may serve as a normalization control. However, it is recognized that hybridization efficiency varies with base composition and probe length. Preferred normalization probes are selected to reflect the average length of the other probes present in the array, however, they can be selected to cover a range of lengths. The normalization control(s) can also be selected to reflect the (average) base composition of the other probes in the array, however in a preferred embodiment, only one or a few normalization probes are used and they are selected such that they hybridize well (i.e. no secondary structure) and do not match any target-specific probes.

Expression level controls are probes that hybridize specifically with constitutively expressed genes in the biological sample. Virtually any constitutively expressed gene provides a suitable target for expression level controls. Typically expression level control probes have sequences complementary to subsequences of constitutively expressed "housekeeping genes" including, but not limited to the β-actin gene, the transferrin receptor gene, the GAPDH gene, and the like.

Mismatch controls may also be provided for the probes to the target genes, for expression level controls or for normalization controls. Mismatch controls are oligonucleotide probes or other nucleic acid probes identical to their corresponding test or control probes except for the presence of one or more mismatched bases. A mismatched base is a base selected so that it is not complementary to the corresponding base in the target sequence to which the probe would otherwise specifically hybridize. One or more mismatches are selected such that under appropriate hybridization conditions (e.g. stringent conditions) the test or control probe would be expected to hybridize with its target sequence, but the mismatch probe would not hybridize (or would hybridize to a significantly lesser extent). Preferred mismatch probes contain a central mismatch. Thus, for example, where a probe is a 20 mer, a corresponding mismatch probe will have the identical sequence except for a single base mismatch (e.g., substituting a G, a C or a T for an A) at any of positions 6 through 14 (the central mismatch).

Mismatch probes thus provide a control for non-specific binding or cross-hybridization to a nucleic acid in the sample other than the target to which the probe is directed. Mismatch probes thus indicate whether a hybridization is specific or not. For example, if the target is present the perfect match probes should be consistently brighter than the mismatch probes. In addition, if all central mismatches are present, the mismatch probes can be used to detect a mutation. The difference in intensity between the perfect match and the mismatch probe (I(PM)-I(MM)) provides a good measure of the concentration of the hybridized material.

The high density array may also include sample preparation/amplification control probes. These are probes that are complementary to subsequences of control genes selected because they do not normally occur in the nucleic acids of the particular biological sample being assayed. Suitable sample preparation/amplification control probes include, for example, probes to bacterial genes (e.g., Bio B) where the sample in question is a biological from a eukaryote.

The RNA sample is then spiked with a known amount of the nucleic acid to which the sample preparation/ amplification control probe is directed before processing. Quantification of the hybridization of the sample preparation/amplification control probe then provides a measure of alteration in the abundance of the nucleic acids caused by processing steps (e.g. PCR, reverse transcription, in vitro transcription, etc.).

In a preferred embodiment, oligonucleotide probes in the high density array are selected to bind specifically to the nucleic acid target to which they are directed with minimal non-specific binding or cross-hybridization under the particular hybridization conditions utilized. Because the high density arrays of this invention can contain in excess of 1,000,000 different probes, it is possible to provide every probe of a characteristic length that binds to a particular nucleic acid sequence. Thus, for example, the high density array can contain every possible 20-mer sequence complementary to an IL-2 mRNA.

However, there may exist 20-mer subsequences that are not unique to the IL-2 mRNA. Probes directed to these subsequences are expected to cross-hybridize with occurrences of their complementary sequence in other regions of the sample genome. Similarly, other probes simply may not hybridize effectively under the hybridization conditions (e.g., due to secondary structure, or interactions with the substrate or other probes). Thus, in a preferred embodiment, the probes that show such poor specificity or hybridization efficiency are identified and may not be included either in the high density array itself (e.g., during fabrication of the array) or in the post-hybridization data analysis.

In addition, in a preferred embodiment, expression monitoring arrays are used to identify the presence and expression (transcription) level of genes which are several hundred base pairs long. For most applications it would be useful to identify the presence, absence, or expression level of several thousand to one hundred thousand genes. Because the number of oligonucleotides per array is limited in a preferred embodiment, it is desired to include only a limited set of probes specific to each gene whose expression is to be detected.

As disclosed in U.S. application Ser. No. 08/72,376, probes as short as 15, 20, or 25 nucleotide are sufficient to hybridize to a subsequence of a gene and that, for most genes, there is a set of probes that performs well across a wide range of target nucleic acid concentrations. In a preferred embodiment, it is desirable to choose a preferred or "optimum" subset of probes for each gene before synthesizing the high density array.

2. Forming High Density Arrays.

Methods of forming high density arrays of oligonucleotides, peptides and other polymer sequences with a minimal number of synthetic steps are known. The oligonucleotide analogue array can be synthesized on a solid substrate by a variety of methods, including, but not limited to, light-directed chemical coupling, and mechanically directed coupling. See Pirrung et al., U.S. Pat. No. 5,143,854 (see also PCT Application No. WO 90/15070) and Fodor et al., PCT Publication Nos. WO 92/10092 and WO 93/09668 and U.S. Ser. No. 07/980,523 which disclose methods of forming vast arrays of peptides, oligonucleotides and other molecules using, for example, light-directed synthesis techniques. See also, Fodor et al., Science, 251, 767–77 (1991). These procedures for synthesis of polymer arrays are now referred to as VLSIPS™ procedures. Using the VLSIPS™ approach, one heterogeneous array of polymers is converted, through simultaneous coupling at a number of reaction sites, into a different heterogeneous array. See, U.S. application Ser. Nos. 07/796,243 and 07/980,523.

The development of VLSIPS™ technology as described in the above-noted U.S. Pat. No. 5,143,854 and PCT patent publication Nos. WO 90/15070 and 92/10092, is considered pioneering technology in the fields of combinatorial synthesis and screening of combinatorial libraries. More recently, patent application Ser. No. 08/082,937, filed Jun. 25, 1993, describes methods for making arrays of oligonucleotide probes that can be used to check or determine a partial or complete sequence of a target nucleic acid and to detect the presence of a nucleic acid containing a specific oligonucleotide sequence.

In brief, the light-directed combinatorial synthesis of oligonucleotide arrays on a glass surface proceeds using automated phosphoramidite chemistry and chip masking techniques. In one specific implementation, a glass surface is derivatized with a silane reagent containing a functional group, e.g., a hydroxyl or amine group blocked by a photolabile protecting group. Photolysis through a photolithographic mask is used selectively to expose functional groups which are then ready to react with incoming 5'-photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface. Combinatorial synthesis of different oligonucleotide analogues at different locations on the array is determined by the pattern of illumination during synthesis and the order of addition of coupling reagents.

In the event that an oligonucleotide analogue with a polyamide backbone is used in the VLSIPS™ procedure, it is generally inappropriate to use phosphoramidite chemistry to perform the synthetic steps, since the monomers do not attach to one another via a phosphate linkage. Instead, peptide synthetic methods are substituted. See, e.g., Pirrung et al. U.S. Pat. No. 5,143,854.

Peptide nucleic acids are commercially available from, e.g., Biosearch, Inc. Bedford, Mass.) which comprise a polyamide backbone and the bases found in naturally occurring nucleosides. Peptide nucleic acids are capable of binding to nucleic acids with high specificity, and are considered "oligonucleotide analogues" for purposes of this disclosure.

In addition to the foregoing, additional methods which can be used to generate an array of oligonucleotides on a single substrate are described in co-pending applications Ser. No. 07/980,523, filed Nov. 20, 1992, and 07/796,243, filed Nov. 22, 1991 and in PCT Publication No. WO 93/09668. In the methods disclosed in these applications, reagents are delivered to the substrate by either (1) flowing within a channel defined on predefined regions or (2) "spotting" on predefined regions or (3) through the use of photoresist. However, other approaches, as well as combinations of spotting and flowing, may be employed. In each instance, certain activated regions of the substrate are mechanically separated from other regions when the monomer solutions are delivered to the various reaction sites.

A typical "flow channel" method applied to the compounds and libraries of the present invention can generally be described as follows. Diverse polymer sequences are synthesized at selected regions of a substrate or solid support by forming flow channels on a surface of the substrate through which appropriate reagents flow or in which appropriate reagents are placed. For example, assume a monomer "A" is to be bound to the substrate in a first group of selected regions. If necessary, all or part of the surface of the substrate in all or a part of the selected regions is activated for binding by, for example, flowing appropriate reagents through all or some of the channels, or by washing the entire substrate with appropriate reagents. After placement of a channel block on the surface of the substrate, a reagent having the monomer A flows through or is placed in all or some of the channel(s). The channels provide fluid contact to the first selected regions, thereby binding the monomer A on the substrate directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the substrate; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form a vast array of sequences of desired length at known locations on the substrate.

After the substrate is activated, monomer A can be flowed through some of the channels, monomer B can be flowed through other channels, a monomer C can be flowed through still other channels, etc. In this manner, many or all of the reaction regions are reacted with a monomer before the channel block must be moved or the substrate must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the substrate. For example, according to some embodiments, a protective coating such as a hydrophilic or hydrophobic coating (depending upon the nature of the solvent) is utilized over portions of the substrate to be protected, sometimes in combination with materials that facilitate wetting by the reactant solution in other regions. In this manner, the flowing solutions are further prevented from passing outside of their designated flow path.

High density nucleic acid arrays can be fabricated by depositing presynthezied or natural nucleic acids in predined positions. Synthesized or natural nucleic acids are deposited on specific locations of a substrate by light directed targeting and oligonucleotide directed targeting. Nucleic acids can also be directed to specific locations in much the same manner as the flow channel methods. For example, a nucleic acid A can be delivered to and coupled with a first group of reaction regions which have been appropriately activated. Thereafter, a nucleic acid B can be delivered to and reacted with a second group of activated reaction regions. Nucleic acids are deposited in selected regions. Another embodiment uses a dispenser that moves from region to region to deposit nucleic acids in specific spots. Typical dispensers include a micropipette or capillary pin to deliver nucleic acid to the substrate and a robotic system to control the position of the micropipette with respect to the substrate. In other embodiments, the dispenser includes a series of tubes, a manifold, an array of pipettes or capillary pins, or the like so that various reagents can be delivered to the reaction regions simultaneously.

3. Hybridization

Nucleic acid hybridization simply involves contacting a probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency in this case in 6×SSPE-T at 37 C. (0.005% Triton X-100) to ensure hybridization and then subsequent washes are performed at higher stringency (e.g., 1×SSPE-T at 37 C.) to eliminate mismatched hybrid duplexes. Successive washes may be performed at increasingly higher stringency (e.g., down to as low as 0.25× SSPE-T at 37 C. to 50 C.) until a desired level of hybridization specificity is obtained. Stringency can also be increased by addition of agents such as formamide. Hybridization specificity may be evaluated by comparison of hybridization to the test probes with hybridization to the various controls that can be present (e.g., expression level control, normalization control, mismatch controls, etc.).

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular oligonucleotide probes of interest.

In a preferred embodiment, background signal is reduced by the use of a detergent (e.g., C-TAB) or a blocking reagent (e.g., sperm DNA, cot-1 DNA, etc.) during the hybridization to reduce non-specific binding. In a particularly preferred embodiment, the hybridization is performed in the presence of about 0.5 mg/ml DNA (e.g., herring sperm DNA). The use of blocking agents in hybridization is well known to those of skill in the art (see, e.g., Chapter 8 in P. Tijssen, supra.)

The stability of duplexes formed between RNAs or DNAs are generally in the order of RNA:RNA>RNA:DNA>DNA:DNA, in solution. Long probes have better duplex stability with a target, but poorer mismatch discrimination than shorter probes (mismatch discrimination refers to the measured hybridization signal ratio between a perfect match probe and a single base mismatch probe). Shorter probes (e.g. 8-mers) discriminate mismatches very well, but the overall duplex stability is low.

Altering the thermal stability ($T_m$) of the duplex formed between the target and the probe using, e.g., known oligonucleotide analogues allows for optimization of duplex stability and mismatch discrimination. One useful aspect of altering the $T_m$ arises from the fact that adenine-thymine (A-T) duplexes have a lower $T_m$ than guanine-cytosine (G-C) duplexes, due in part to the fact that the A-T duplexes have 2 hydrogen bonds per base-pair, while the G-C duplexes have 3 hydrogen bonds per base pair. In heterogeneous oligonucleotide arrays in which there is a non-uniform distribution of bases, it is not generally possible to optimize hybridization for each oligonucleotide probe simultaneously. Thus, in some embodiments, it is desirable to selectively destabilize G-C duplexes and/or to increase the stability of A-T duplexes. This can be accomplished, e.g., by substituting guanine residues in the probes of an array which form G-C duplexes with hypoxanthine, or by substituting adenine residues in probes which form A-T duplexes with 2,6 diaminopurine or by using the salt tetramethyl ammonium chloride (TMACl) in place of NaCl.

Altered duplex stability conferred by using oligonucleotide analogue probes can be ascertained by following, e.g., fluorescence signal intensity of oligonucleotide analogue arrays hybridized with a target oligonucleotide over time. The data allow optimization of specific hybridization conditions at, e.g., room temperature (for simplified diagnostic applications in the future).

Another way of verifying altered duplex stability is by following the signal intensity generated upon hybridization with time. Previous experiments using DNA targets and DNA chips have shown that signal intensity increases with time, and that the more stable duplexes generate higher signal intensities faster than less stable duplexes. The signals reach a plateau or "saturate" after a certain amount of time due to all of the binding sites becoming occupied. These data allow for optimization of hybridization, and determination of the best conditions at a specified temperature.

Methods of optimizing hybridization conditions are well known to those of skill in the art (see, e.g., *Laboratory Techniques in Biochemistry and Molecular Biology, Vol. 24: Hybridization With Nucleic Acid Probes*, P. Tijssen, ed. Elsevier, N.Y., (1993)).

(C) Signal Detection

In a preferred embodiment, the hybridized nucleic acids are detected by detecting one or more labels attached to the sample nucleic acids. The labels may be incorporated by any of a number of means well known to those of skill in the art. However, in a preferred embodiment, the label is simultaneously incorporated during the amplification step in the preparation of the sample nucleic acids. Thus, for example, polymerase chain reaction (PCR) with labeled primers or labeled nucleotides will provide a labeled amplification product. In a preferred embodiment, transcription amplification, as described above, using a labeled nucleotide (e.g. fluorescein-labeled UTP and/or CTP) incorporates a label into the transcribed nucleic acids.

Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label. One particular preferred methods uses colloidal gold label that can be detected by measuring scattered light.

The label may be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an aviden-conjugated fluorophore will bind the biotin bearing hybrid duplexes providing a label that is easily detected. For a detailed review of methods of labeling nucleic acids and detecting labeled hybridized nucleic acids see *Laboratory Techniques in Biochemistry and Molecular Biology, Vol. 24: Hybridization With Nucleic Acid Probes*, P. Tijssen, ed. Elsevier, N.Y., (1993)).

Fluorescent labels are preferred and easily added during an in vitro transcription reaction. In a preferred embodiment, fluorescein labeled UTP and CTP are incorporated into the RNA produced in an in vitro transcription reaction as described above.

Means of detecting labeled target (sample) nucleic acids hybridized to the probes of the high density array are known to those of skill in the art. Thus, for example, where a colorimetric label is used, simple visualization of the label is sufficient. Where a radioactive labeled probe is used, detection of the radiation (e.g. with photographic film or a solid state detector) is sufficient.

In a preferred embodiment, however, the target nucleic acids are labeled with a fluorescent label and the localization of the label on the probe array is accomplished with fluorescent microscopy. The hybridized array is excited with a light source at the excitation wavelength of the particular fluorescent label and the resulting fluorescence at the emission wavelength is detected. In a particularly preferred embodiment, the excitation light source is a laser appropriate for the excitation of the fluorescent label.

The confocal microscope may be automated with a computer-controlled stage to automatically scan the entire high density array. Similarly, the microscope may be equipped with a phototransducer (e.g., a photomultiplier, a solid state array, a CCD camera, etc.) attached to an automated data acquisition system to automatically record the fluorescence signal produced by hybridization to each oligonucleotide probe on the array. Such automated systems are described at length in U.S. Pat. No: 5,143,854, PCT Application 20 92/10092, and copending U.S. application Ser. No. 08/195,889 filed on Feb. 10, 1994. Use of laser illumination in conjunction with automated confocal microscopy for signal detection permits detection at a resolution of better than about 100 $\mu$m, more preferably better than about 50 $\mu$m, and most preferably better than about 25 $\mu$m.

One of skill in the art will appreciate that methods for evaluating the hybridization results vary with the nature of the specific probe nucleic acids used as well as the controls provided. In the simplest embodiment, simple quantification of the fluorescence intensity for each probe is determined. This is accomplished simply by measuring probe signal strength at each location (representing a different probe) on the high density array (e.g., where the label is a fluorescent label, detection of the amount of florescence (intensity) produced by a fixed excitation illumination at each location on the array). Comparison of the absolute intensities of an array hybridized to nucleic acids from a "test" sample with intensities produced by a "control" sample provides a measure of the relative expression of the nucleic acids that hybridize to each of the probes.

One of skill in the art, however, will appreciate that hybridization signals will vary in strength with efficiency of hybridization, the amount of label on the sample nucleic acid and the amount of the particular nucleic acid in the sample.

Typically nucleic acids present at very low levels (e.g., <1 pM) will show a very weak signal. At some low level of concentration, the signal becomes virtually indistinguishable from background. In evaluating the hybridization data, a threshold intensity value may be selected below which a signal is not counted as being essentially indistinguishable from background.

Where it is desirable to detect nucleic acids expressed at lower levels, a lower threshold is chosen. Conversely, where only high expression levels are to be evaluated a higher threshold level is selected. In a preferred embodiment, a suitable threshold is about 10% above that of the average background signal.

In addition, the provision of appropriate controls permits a more detailed analysis that controls for variations in hybridization conditions, cell health, non-specific binding and the like. Thus, for example, in a preferred embodiment, the hybridization array is provided with normalization controls. These normalization controls are probes complementary to control sequences added in a known concentration to the sample. Where the overall hybridization conditions are poor, the normalization controls will show a smaller signal reflecting reduced hybridization. Conversely, where hybridization conditions are good, the normalization controls will provide a higher signal reflecting the improved hybridization. Normalization of the signal derived from other probes in the array to the normalization controls thus provides a control for variations in hybridization conditions. Typically, normalization is accomplished by dividing the measured signal from the other probes in the array by the average signal produced by the normalization controls. Normalization may also include correction for variations due to sample preparation and amplification. Such normalization may be accomplished by dividing the measured signal by the average signal from the sample preparation/amplification control probes (e.g., the Bio B probes). The resulting values may be multiplied by a constant value to scale the results.

As indicated above, the high density array can include mismatch controls. In a preferred embodiment, there is a mismatch control having a central mismatch for every probe (except the normalization controls) in the array. It is expected that after washing in stringent conditions, where a perfect match would be expected to hybridize to the probe, but not to the mismatch, the signal from the mismatch controls should only reflect non-specific binding or the presence in the sample of a nucleic acid that hybridizes with the mismatch. Where both the probe in question and its corresponding mismatch control both show high signals, or the mismatch shows a higher signal than its corresponding test probe, there is a problem with the hybridization and the signal from those probes is ignored. The difference in hybridization signal intensity between the target specific probe and its corresponding mismatch control is a measure of the discrimination of the target-specific probe. Thus, in a preferred embodiment, the signal of the mismatch probe is subtracted from the signal from its corresponding test probe to provide a measure of the signal due to specific binding of the test probe.

The concentration of a particular sequence can then be determined by measuring the signal intensity of each of the probes that bind specifically to that gene and normalizing to the normalization controls. Where the signal from the probes is greater than the mismatch, the mismatch is subtracted. Where the mismatch intensity is equal to or greater than its corresponding test probe, the signal is ignored. The expression level of a particular gene can then be scored by the number of positive signals (either absolute or above a threshold value), the intensity of the positive signals (either absolute or above a selected threshold value), or a combination of both metrics (e.g., a weighted average).

In some preferred embodiments, a computer system is used to compare the hybridization intensities of the perfect match and mismatch probes of each pair. If the gene is expressed, the hybridization intensity (or affinity) of a perfect match probe of a pair should be recognizably higher than the corresponding mismatch probe. Generally, if the hybridizations intensities of a pair of probes are substantially the same, it may indicate the gene is not expressed. However, the determination is not based on a single pair of probes, the determination of whether a gene is expressed is based on an analysis of many pairs of probes.

After the system compares the hybridization intensity of the perfect match and mismatch probes, the system indicates expression of the gene. As an example, the system may indicate to a user that the gene is either present (expressed), marginal or absent (unexpressed). Specific procedures for data analysis is disclosed in U.S. application Ser. No. 08/772,376, previously incorporated for all purposes.

In addition to high density nucleic acid arrays, other methods are also useful for massive gene expression monitoring. Differential display, described by Liang, P. and Pardee, A. B. (Differential Display of eukaryotic messenger RNA by means of the polymerase chain reaction. *Science* 257:967–971, 1992, incorporated herein by reference for all purposes) provides a useful mean for distinguishing gene expression between two samples. Serial analysis of gene expression, described by Velculescu et al. (Serial Analysis of Gene Expression. Science, 270:484–487, 1995, incorporated herein by reference for all purposes) provides another method for quantative and qualitative analysis of gene expression. Optical fiber oligonucleotide sensors, described by Ferguson et al. (A Fiber-optic DNA biosensor microarray for the analysis of gene expression. Nature-Biotechnology 14:1681–1684, 1996), can also be used for gene expression monitoring.

V. Genetic Network and Interrogating the Genetic Network by Expression Monitoring As indicated above, the regulation of transcription, RNA processing and RNA editing are all accomplished by proteins which are coded by their own genes. In addition, DNA sequences can exert long range control over the expression of other genes by positional effects. Therefore, the expression of genes is often regulated by the expression of other genes. Those regulatory genes are called up-stream genes, relative to the regulated or down-stream genes. In a simple regulatory pathway:

where:

A, B, C, D are genes

++ up-regulates

-- down-regulates

Gene A is an up-stream gene of gene B and B is an up-stream gene of C. One of skill in the art would appreciate that the network is frequently looped and inter-connected. In some instance, the expression of a gene is regulated by its own product as either a positive or negative feedback (FIG. 1 illustrates a hypothetical gene network).

Traditionally, the genetic network is studied by isolating a particular gene or a pathway of genes and understanding the regulation of one or at most few genes. One aspect of this invention is to provide a systematic approach to understand the regulatory relationship among genes in the entire genetic network in many or all species. This approach is premised, in part, on the development of methods for massive parallel monitoring of gene expression. The current invention is also premised, in part, upon the availability of biological samples reflecting the genetic network in various of stages and states. By observing the change of gene expression, the regulatory relationship can be defined with various data processing methods. Because of the complexity of the genetic network, those of skill in the art would appreciate the importance of obtaining a large number of biological samples reflecting various stages of the genetic network. Cultured cells or tissue samples reflecting various physiological, developmental, pathological states are useful because they reflect independent states of the genetic network. One aspect of the invention provides methods to generate a large number of additional biological samples reflecting a massive number of independent states of the genetic network.

A. Artificial cell lines.

In some embodiments, a cell line is treated with mutagens, radiation, virus infection, or transcription vectors. Treated cells are then cloned and propagated to produce sufficient amount of mRNA. Each clone reflect an independent state of gene expression. In some other embodiments, more sophisticated methods of genetic mutation is used for systematically knocking out genes. Methods such as the Random Homozygous Knock-out are particularly preferred because of their efficiency in obtaining homozygous knock out cells.

1) Chemical and Irradiation Mutagenesis

Exposure to mutagenic chemicals, such as ethyl nitrorsurea and ethyl methylsulfonate or to high dose of X-rays can be used to produced a large number mutant cells. Such mutagenesis is essentially random, even though some mutants may not survive and thus will not be represented in the final clones. Clone mutant cells will have different profiles of gene expression.

2) Antisense Oligonucleotides

Oligonucleotides with sequence complementary to a mRNA sequence can be introduced into cells to block the translation of the mRNA, thus blocking the function of the gene encoding the mRNA. The use of oligonucleotides to block gene expression is preferred in some embodiments because of the simplicity of its procedure. The use of oligonucleotides to block gene expression is described, for example, in, Strachan and Read, Human Molecular Genetics, 1996, previously incorporated by reference for all purposes.

3) Antisense Genes

Specially designed vectors containing antisense genes can be stably transfected into cells to produce antisense RNA to block gene expression. In some embodiments, an antisense minigene is constructed by cloning a DNA sequence complementary to the mRNA targeted. The DNA sequence is under the control of a promoter sequence at one end and enclosed with a polyadenylation sequence at the other end. Transcription from such a vector produces an antisense RNA which blocks the function of the targeted mRNA.

B. Statistical analysis.

The purpose of statistical analysis is to establish and test causal models for the genetic network. It is apparent to those skilled in the art that those causal models can be used to generate dynamic maps of regulatory pathways. A variety of statistical methods that have been developed for understanding complex systems are useful for some of the embodiments. In some embodiments, cluster analysis methods are used to group genes whose expression level is correlated. Methods for cluster analysis are described in detail in Hartigan (1975) *Clustering Algorithms,* NY, John Wile and Sons, Inc, and Everritt, (1980) *Cluster Analysis* 2nd. Ed. London Heineman Educational books, Ltd., incorporated herein for all purposed by reference. The causal relationships in a genetic network can also be modeled by stochastic procedures. Such models allow the examination of the dynamical aspects of the genetic network in terms of change over time or across conditions. Maybeck, *Stochastic Models, estimation and control,* vol. 1. (1979) NY, Academic Press.

Directional, correlational, and causation models of gene regulation can be built based upon the level of expression of different genes. In some embodiments, models are built by incorporating expression data and current knowledge about the regulation of specific genes. Path analysis can be used to decomposing relations among variables and for testing causal models for genetic networks. However, path analysis is generally limited by its assumptions, such as variables measured withour error, no correlation among residuals and unidirectional causal flow.

Linear Structural Relationship Analysis (LISREL) is particularly preferred for testing the statistical confidence of such models because it overcomes many of the limitations of path analysis methods. LISREL is a very general approach for causal model analysis. It allows latent or hidden (not measurable) variables. Therefore, in some embodiments, latent variables are used to account for unmeasured genes or regulatory relations. LISREL models also allow bidirectional or reciprocal causation, measurement errors and correlated residuals. Mathematical theories and applications of LISREL are described in detail in Joreskog and Sorbom (1979) *Advances in Factor Analysis and Structual Equations Modeling,* Cambridge Mass., Abt Books; and Joreskog and Sorbom, (1985) *LISREL, VI: Analysis of Linear Structural Relationships by Maximum Liklihood Insturmental Variables and Least Squares,* Uppsala, Sweden: University of Uppsala, incorporated herein by reference for all purposes. Computer implementations of LISREL are provided by numerous other software packages.

One of skill in the art would appreciate that other causal model methods are also appropriate for analyszing gene expression data. Structure models are reviewed by Bentler, P. M. Multivariate Analysis with Latent Variables: Causal Modeling, Ann. Rev. Psychol. 31:419–56 (1980)

VI. Identifying the Function of a Gene or a Mutation by Expression Monitoring

Figure 3:
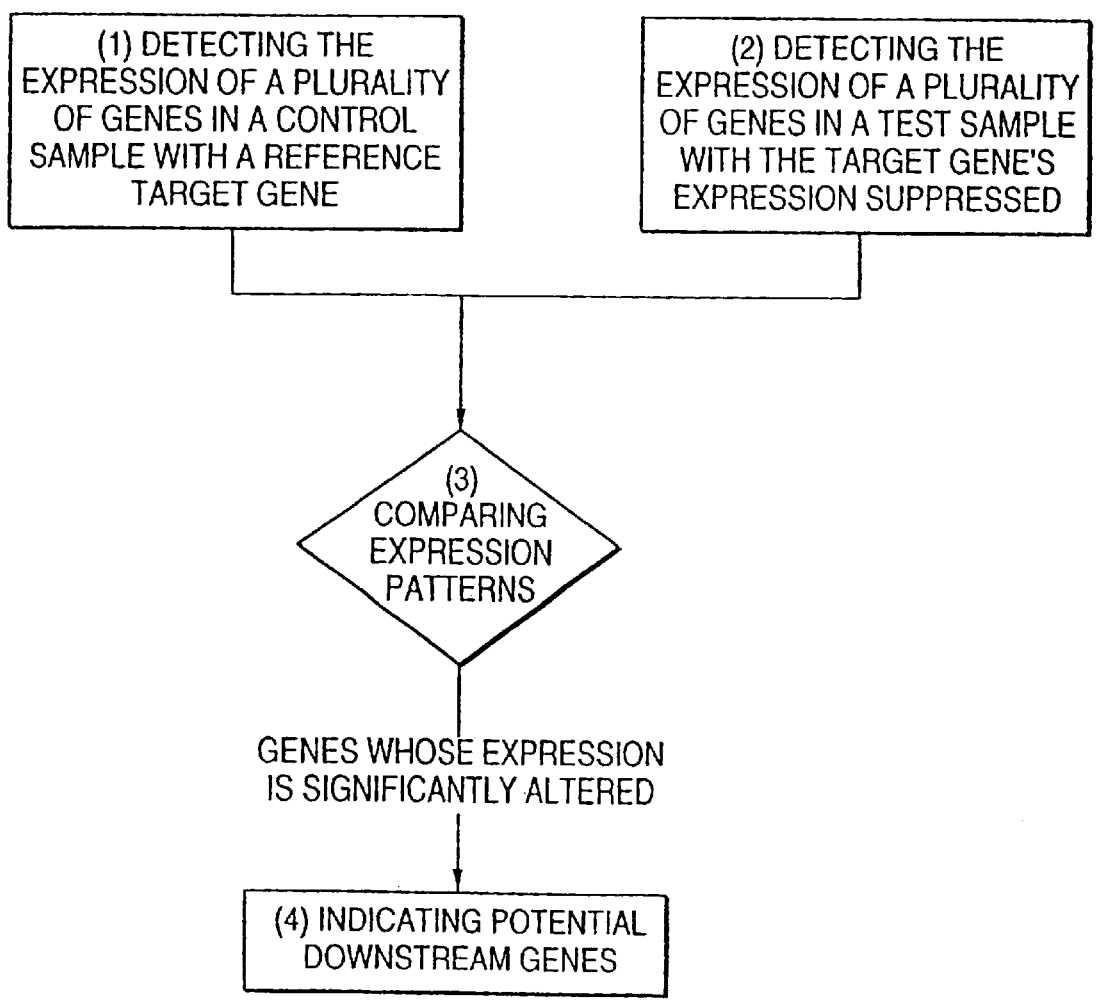
FIG. 3 shows a schematic of one embodiment for expression monitoring for gene function identification.

One aspect of the invention provides methods for detecting regulatory functions of a gene by identifying whether or not the target gene regulates the expression of other genes. FIG. 3 illustrates one embodiment of such a method. In some embodiments, the gene of interest is mutated or its functions repressed by other means (2). A variety of methods can be used to specifically suppress the expression of a target gene, including the use of antisense oligonucleotides and antisense genes. In some other embodiments, the gene of interest is introduced to a cell that lacks the expression of the gene of interest and the expression of a large number of genes is monitored to detect in the alteration of expression pattern. Cell lines are preferred for studying the regulatory function of a target gene in some embodiments because of low cost of maintenance and construction.

The expression of a large number of genes, preferably more than 10, more preferably more than 100, and most preferably more than 1000 genes, is monitored to detect significant changes in the pattern of expression (1,2). The change in expression is then analyzed to detect the specific genes that are potentially regulated by the gene of interest (3).

The expression level of down-stream genes is often not directly correlated with the expression of up-stream genes. For example, an up-stream gene encoding a transcriptional factor that regulates a down-stream gene may be expressed at a constant rate. The regulation of down-stream gene activity is through changes in the transcriptional factor activity by binding to a signal molecule, not through changes in the amount of the transcriptional factor. It would be difficult to interpret the regulatory relationship solely based upon the correlation between the activity of two genes. To overcome this complication, in some embodiments, the target gene is completely suppressed for a certain period of time to deplete any reserve of gene products.

Another complication is due to the redundancy of regulatory genes. For example, a regulatory gene may be suppressed and no change in the expression of down-stream genes occur because redundant genes perform a similar function as the target gene. Therefore, no change in the expression profile by suppressing a target gene may not give a definitive answer as to whether the target gene has regulatory functions.

Figure 4:
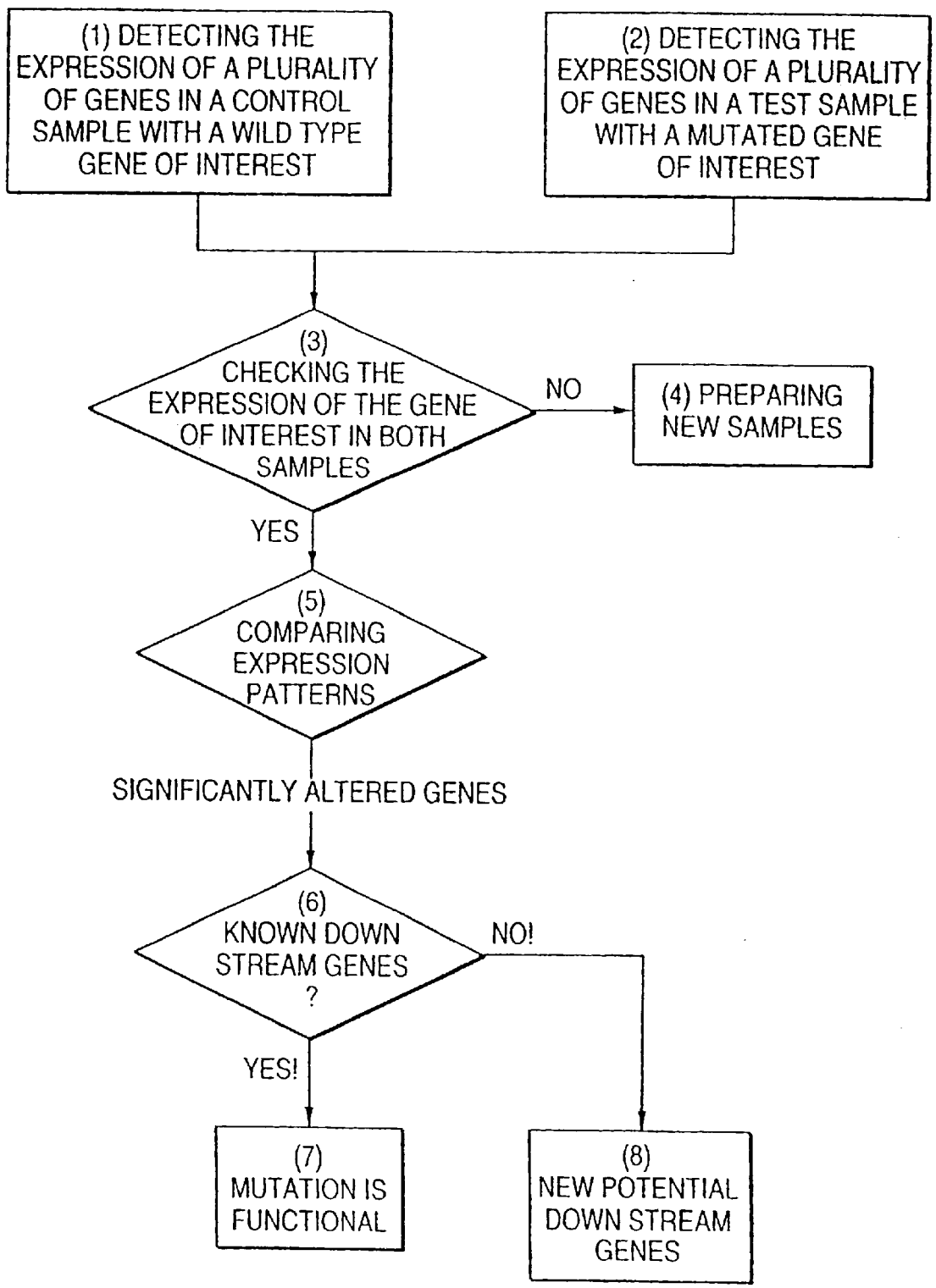
FIG. 4 shows a schematic of one embodiment for expression monitoring for mutation function identification.

Similarly, the function of a mutation in a regulatory gene can be identified by gene expression monitoring. FIG. 4 illustrates one such embodiment. In some embodiments, nucleic acid samples from a wild-type biological sample (1) and from a mutant (2) are analyzed to obtain wild-type and mutant expression profile of several down-stream genes. A change in the expression of down-stream gene may indicate that the mutation is not silent. (7).

Because of complicating factors discussed above and experimental variations, it is preferable to monitor the expression of several down-stream genes. In one particular embodiment, the function of p53 mutation is determined by monitoring the expression of p53 up-regulated gadd45, cyclin G, p21waf1, Bax, IGF-BP3 and Thrombospondin genes and p53 down regulated c-myc and PCNA genes. The inclusion of more regulated genes improves the quality and reliability of the analysis.

EXAMPLE 1

Identification of Phenotype of a p53 Mutation

Mutations of the p53 gene are the most commonly found abnormality in human cancer (Volgelstein, 1990, A deadly inheritance. *Nature* 348:681–2). A recent compilation and analysis of screening data indicated that 37% of the 2567 cancers contained mutations in the p53 gene (Greenblatt et al., 1994, Mutations in the p53 tumor suppressor gene: clues to cancer etiology and molecular pathogenesis. *Cancer Res.* 54:4855–78).

The high association between p53 mutations and many forms of cancer suggests that loss of p53 function can be used as a marker for high susceptibility to cacinogenesis. Direct sequence analysis of the p53 gene could theoretically detect all mutations. However, not all mutations have functional significance. Detection of the loss of p53 function is, however, a challenging task. Immunohistochemistry (IHC) methods can be used to detect some forms of dysfunctional p53 mutant proteins. The IHC detection method relies upon the fact that the amount of mutant p53 is increased in tumor cells with p53 dysfunction (Nigro, J M, Baker, S J, Preisinger, A C, Jessup, J M, Hostetter, R, Cleary, K. et al., Mutations in the p53 gene occur in diverse human tumor types. Nature 1989; 342:705–8). This increase in the amount of mutant p53 is probably due to an increased half-life of the mutant p53, compared with its wild-type form. However, nonsense mutations, which lead to truncated forms of p53, do not result in the increase of p53 concentration. One aspect of the invention overcomes these shortcomings of the prior art, by providing a method for identifying the loss of p53 function in a cell.

1. High Density Array Design and Fabrication

Using photolithography and solid phase chemical synthesis, specified DNA probes on derivitized glass at a density of $10^7$ oligonucleotide molecules per 50 mm$^2$ synthesis region were synthesized. Methods of light directed solid phase synthesis is described elsewhere in the application.

Approximately 65,000 unique DNA probes ($10^7$ unique probes/50 mm$^2$ area) were synthesized on a 1.2 cm$^2$ glass slide. A set of 4 different oligonucleotide arrays that include more than 6,500 human gene sequences derived from the GenBank and dbEST databases were generated. These arrays were used to monitor and compare the expression of >6,500 genes in parallel from normal and malignant breast tissue cell lines.

2. Preparation of Wild-type and Mutant p53 Sample

Figure 5:
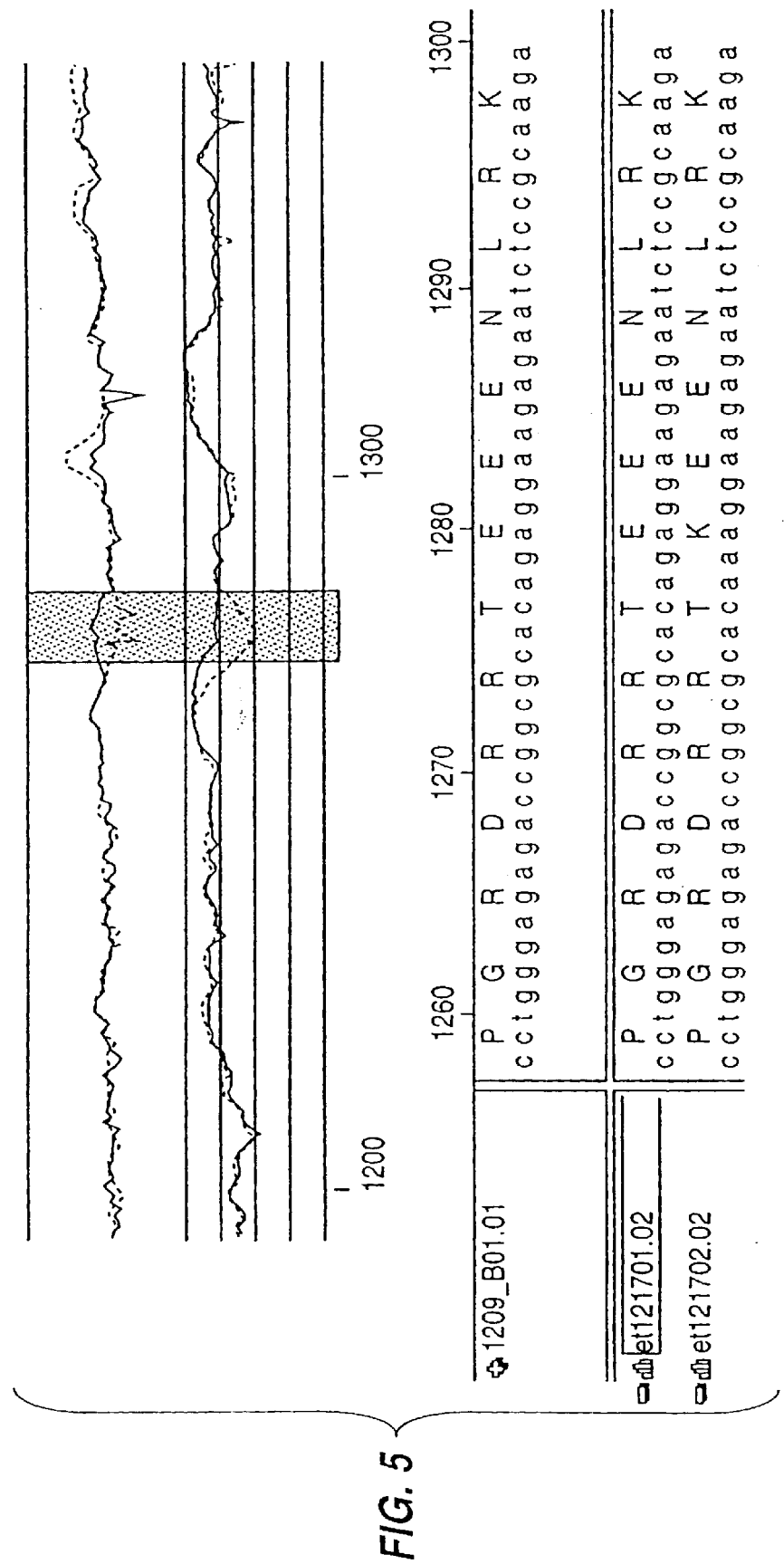
FIG. 5 shows the result of GeneChip® sequence analysis of p53 genes in normal and malignant breast epithelium cells.

Labeled RNA for array hybridization experiments was derived from the malignant breast cell line BT474 and normal breast tissue from primary cell line HT-125. BT-474 was isolated from a solid, invasive ductal carcinoma of the breast and is tumorigenic in athymic nude mice. HT-125 was obtained from a cell line derived from normal breast tissue peripheral to an infiltrating ductal carcinoma. Using a p53 genotyping array (Affymetrix, Santa Clara, Calif.), the p53 gene in BT-474 was analyzed to find potential mutations. FIG. 5 shows the results of the genotypic analysis demonstrating that there was a G to A base change resulting in a E to K amino acid change at position 285 in exon 8, the p53 DNA binding domain. Methods for this genotypic analysis is disclosed in the U.S. patent application Ser. No. 08/143, 312, filed on Oct. 26, 1993, WO 95/11995, U.S. Pat. No. 5,677,195, U.S. Ser. No. 08/327,525, filed Oct. 21, 1994, and WO 97/29212, incorporated herein by reference for all purposes.

3. Nucleic Acid Sample Preparation

The normal and malignant cells were harvested, lysed and Poly A$^+$ RNA isolated and used as template for double stranded cDNA (ds cDNA) synthesis using an oligo dT primer containing a T7 promoter sequence at its 5' end. ds cDNA product then served as template in an in vitro transcription (IVT) reaction using T7 polymerase and biotinylated ribonucleotides.

3. Hybridization, Data Acquisition and Analysis.

The labeled cRNA was then fragmented in the presence of heat and Mg$^{2+}$ and hybridized to the oligonucleotide arrays in the presence of label control targets used for array normalization and message quantitation. After washing and staining with streptavidin-phycoerythrin conjugate, hybridization patterns were visualized using an argon laser scanning confocal microscope (Affymetix, Santa Clara, Calif.) and the fluorescence intensity images processed and quantitated by GeneSeq software (Affymetrix, Santa Clara, Calif.).

TABLE 1

Gene Expression Monitoring for Mutation Function Identification

| Gene | Function | Expression Level, picomolar (pM) | |
|---|---|---|---|
| | | HT-125 (Normal) | BT474 (Malignant) |
| Transcriptionally activated by p53 | | | |
| Bax | Inducer of apoptosis (bcl-2 associated protein) | 40 ± 3 | undetected |
| Cyclin G | Cell-cycle component | 50 ± 4 | undetected |
| GADD45 | Growth arrest and DNA damage inducible gene | 300 ± 12 | 25 ± 5 |
| IGF-BP3 | Insulin growth factor pathway inhibitor | 4,000 ± 400 | undetected |
| p21$_{WAF1/CIP1}$ | Cyclin-CDK and DNA replication inhibitor | 350 ± 30 | undetected |
| Thrombospondin | Inhibitor of angiogensis | 800 ± 45 | undetected |
| Transcriptionally repressed by p53 | | | |
| c-myc | Cellular oncoprotein | 30 ± 5 | 350 ± 25 |
| PCNA | DNA polymerase processibity factor | 90 ± 10 | 1,000 ± 70 |

Figure 6:
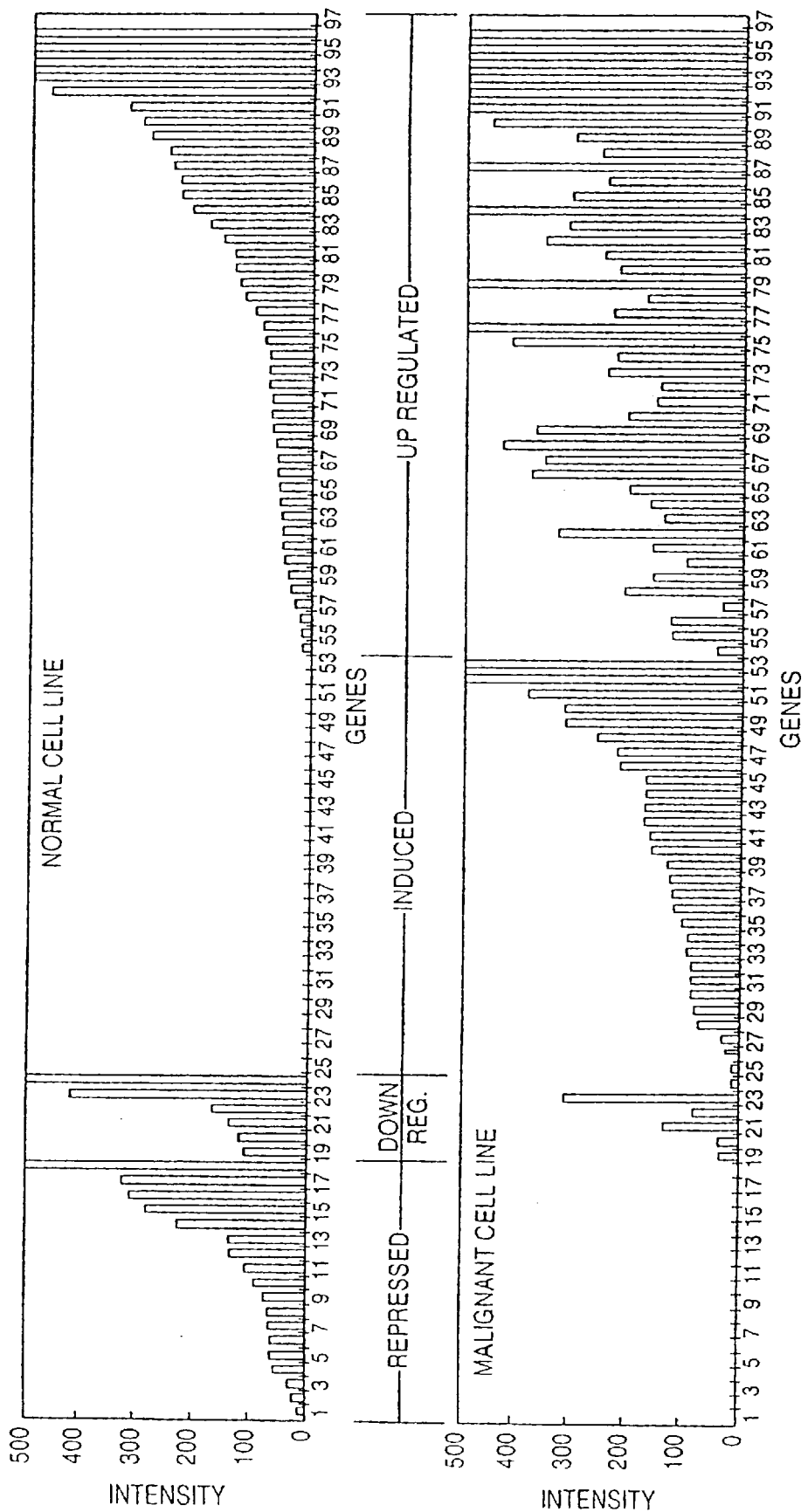
FIG. 6 shows an expression profile of normal and malignant breast epithelium cell.

FIG. 6 shows that the expression of a number of genes is altered in normal and malignant cell lines. Table 1 summarizes the expression of several p53 down-stream genes. The expression level of p53 activated targets gadd45, cyclin G, p21waf1, Bax, IGF-BP3 and Thrombospondin in BT-474 is lost. A coincident gain of expression was seen of the p53 repressed targets c-myc and PCNA. These expression patterns in BT474 indicated a loss of wild-type p53 function. Therefore, the G to A mutation in the p53 gene impairs the regulatory function of the p53 gene.

VII. Mutation Detection by Gene Expression Monitoring

Figure 7:
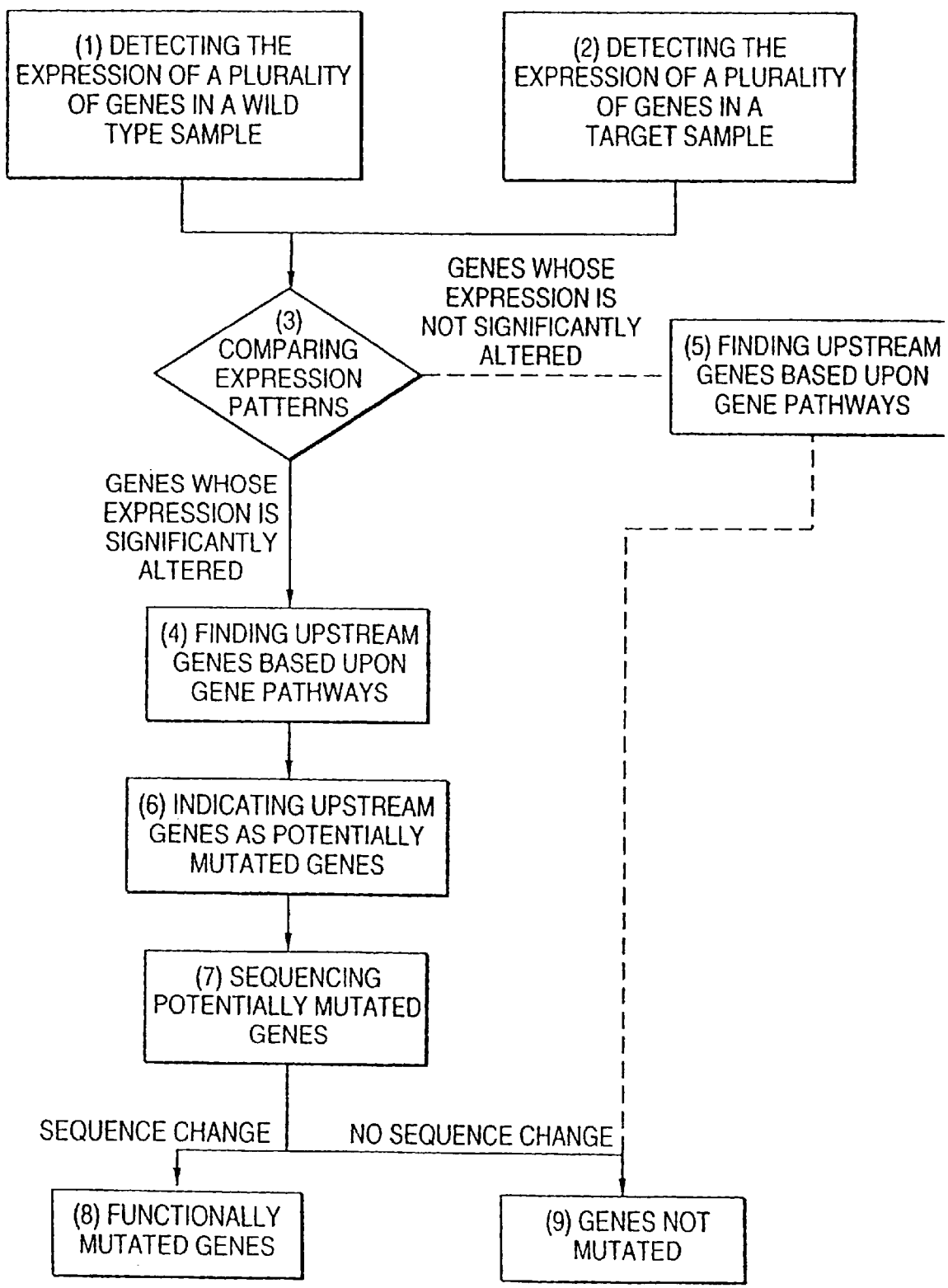
FIG. 7 shows a schematic of one embodiment for expression monitoring for mutation function identification.

In one aspect of the invention, gene expression monitoring is used to detect potential malfunction of regulatory genes, such as a mutation in the coding or regulatory regions. In some embodiments (FIG. 7), the expression of a subset of genes of interest in a diseased tissue is analyzed to obtain a diseased expression pattern (2). The subset contains at least one gene, preferably more than 5 genes, preferably more than 100 genes, more preferably more than 1,000 genes, and most preferably more than 6,000 genes or all the known genes. The expression of the same genes in a normal tissue can also be similarly analyzed to generate a normal gene expression pattern (1). Difference in the expression of genes indicates the abnormality of regulation of changed genes in the diseased tissue (3). In some embodiments, a filter is used to identify those genes whose expression is significantly altered. By using a filter, only those genes whose expression is enhanced or reduced in the diseased tissue by more than 3, 5, or 10-fold are identified as altered. Up-stream genes of the altered genes are indicated as potentially mutated genes (6). In some embodiments, such potenially mutated genes are sequenced to detect sequence changes (9).

Various nucleic acid sequence analysis methods can be used for detecting sequence changes. In one preferred method, high density oligonucleotide arrays are used to detect the sequence changes. One advantage of using oligonucleotide arrays is that the sequence interrogation can be performed in conjunction with gene expression monitoring in a single chip.

It is a suprising discovery that gene expression monitoring can be used to detect heterozygous mutations in regulatory genes, as illustrated by the following example. Therefore, the current invention provides a powerful method for mutation detection.

EXAMPLE 2

Detection of Heterozygous Functional Mutations in the p53 Gene

One aspect of the invention provides a method for detecting mutations in the p53 gene which affect function.

1. High Density Array Design and Fabrication

Using photolithography and solid phase chemical synthesis, specified DNA probes on derivitized glass at a density of $10^7$ oligonucleotide molecules per 50 mm$^2$ synthesis region were synthesized.

Approximately 65,000 unique DNA probes ($10^7$ unique probes/50 mm$^2$ area) were synthesized on a 1.2 cm$^2$ glass slide. A set of 4 different oligonucleotide arrays that include more than 6,500 human gene sequences derived from the GenBank and dbEST databases were generated. These arrays were used to monitor and compare the expression of >6,500 genes in parallel from normal and malignant breast tissue cell lines.

2. Sample Preparation

Labeled RNA for array hybridization experiments was derived from the malignant breast cell line MDA 468 and MDA231 and normal breast tissue from primary cell line HT-125. HT-125 was obtained from a cell line derived from normal breast tissue peripheral to an infiltrating ductal carcinoma. The normal and malignant cells were harvested, lysed and Poly A$^+$ RNA isolated and used as template for double stranded cDNA (ds cDNA) synthesis using an oligo dT primer containing a T7 promoter sequence at its 5' end. ds cDNA product then served as template in an in vitro transcription (IVT) reaction using T7 polymerase and biotinylated ribonucleotides.

3. Hybridization, Data Acquisition and Analysis

The labeled cRNA was then fragmented in the presence of heat and Mg$^{2+}$ and hybridized to the oligonucleotide arrays in the presence of label control targets used for array normalization and message quantitation. After washing and staining with streptavidin-phycoerythrin conjugate, hybridization patterns were visualized using an argon laser scanning confocal microscope (Affymetix, Santa Clara, Calif.) and the fluorescence intensity images processed and quantitated by GeneSeq software (Affymetrix, Santa Clara, Calif.).

From Table 2, the expression of p53 activated targets gadd45, cyclin G, p21waf1, Bax, IGF-BP3 and Thrombospondin in MDA468 and MDA231 is lost. A coincident gain of expression was seen of the p53 repressed targets c-myc and PCNA. These expression patterns in BT-474 indicated a loss of wild-type p53 function in both MDA468 and MDA231. A p53 genotyping array analysis confirmed heterozygous mutations in MDA438 and MDA231.

This example illustrates the ability of gene expression monitoring to detect function-affecting heterozygous mutations. It also provides a powerful and efficient method for detecting p53 function-affecting mutations, including heterozygous and homozygous mutations.

TABLE 2

Gene Expression Monitoring for Functional Mutation Identification

| Gene | Function | Expression Level, picomolar (pM) | | |
|---|---|---|---|---|
| | | HT-125 (Normal) | MDA468 | MDA231 |
| Transcriptionally activated by p53 | | | | |
| Bax | Inducer of apoptosis (bcl-2 associated protein) | 40 ± 5 | undetected | undetected |
| Cyclin G | Cell-cycle component | 50 ± 5 | undetected | undetected |
| GADD45 | Growth arrest and DNA damage inducible gene | 300 ± 15 | 30 ± 5 | undetected |
| IGF-BP3 | Insulin growth factor pathway inhibitor | 4,000 ± 400 | undetected | undetected |
| p21$_{WAF1/CIP1}$ | Cyclin-CDK and DNA replication inhibitor | 350 ± 30 | undetected | undetected |
| Thrombospondin | Inhibitor of angiogensis | 800 ± 45 | undetected | undetected |
| Transcriptionally repressed by p53 | | | | |
| c-myc | Cellular oncoprotein | 30 ± 5 | 350 ± 20 | 500 ± 20 |
| PCNA | DNA polymerase processibity factor | 90 ± 10 | 1,000 ± 50 | 1,000 ± 75 |

EXAMPLE 3

Identification of Differentially Expressed Genes in Breast Tissues

An understanding of the molecular basis of disease requires the ability to detect genetic variation across a large number of genes and to correlate genetic factors with the resulting cellular consequences. The use of high density oligonucleotide (nucleic acid) arrays provided genotyping of candidate genes as well as the characterization of the relative abundance of mRNAs identified herein. Information from the human genome project, Merck EST sequencing effort, or any other source of genetic sequence information may be used to design and fabricate such oligonucleotide arrays for the highly parallel analysis of mRNA levels. DNA arrays containing probes that are complementary to 6,600 human ESTs were used in the particular experiments outlined herein to identify such messenger RNAs. These arrays were used to generate normal and breast cancer specific gene expression profiles. Expression levels of 137 genes increased in malignant breast cells>10-fold compared to normal breast cells. The expression of a further 167 genes decreased to near undetectable levels. A total of 1,549 expressed genes were detected in the breast cancer cells. A simple categorization of the expression changes revealed patterns characteristic of loss of wild-type p53 function, as well as increases in the Her2/neu oncogene and its signal transduction pathway, including Grb-7, Ras, Raf, Mek and ERK. Genotyping of the p53 locus using a DNA re-sequence analysis array revealed inactivating mutations in the p53 DNA binding domain and loss of heterozygosity, consistent with the functional profile given by the expression monitoring array. These data demonstrate how gene expression profiles can be used to characterize the functional state of a cell, and suggest a general array hybridization based approach to decipher specific biochemical pathways and generate new testable hypotheses.

The expressed genes identified herein will find application in a wide array of uses. Included among such uses are diagnostic uses, prognostic uses, therapeutic uses, and forensic uses.

The particular arrays designed herein utilized semiconductor based photolithography and solid phase chemical synthesis to directly synthesize independently specified DNA probes on derivitized glass at a density of $10^7$ oligonucleotide molecules per 50 $\mu m^2$ synthesis region, as discussed in Lockhart, D. J., Dong, H., Byrne, M. C., Follettie, M. T., Gallo, M. V., Chee, M. S., Mittmann, M., Wang, C., Kobayashi, M., Horton, H. & Brown, E. L, Expression monitoring by hybridization to high-density oligonucleotide arrays. Nature Biotechnolog 13, 1675–1680 (1996), incorporated herein by reference. Approximately 65,000 unique 50 $\mu m^2$ synthesis areas were synthesized in parallel on a 1.28 $cm^2$ glass slide. Such high density oligonucleotide arrays applied to gene expression monitoring are specific, sensitive and quantitative, allowing detection of message levels down to one copy per cell. In the particular applications discussed herein oligonucleotide arrays were generated with probes selected from 6,600 EST gene clusters derived from the dbEST public database, as described in Boguski, M. S., Lowe, T. M. & Tolstoshev, C. M. dbEST-database for 'expressed sequence tags'. Nature Genetics 4, 332–333 (1993), incorporated herein by reference. These arrays are complementary to 3,200 human full length GenBank genes, and 3,400 ESTs that demonstrate strong homology to other eukaryotic genes in the SwissProt protein sequence database. Particular arrays herein contained collections of 20 probe pairs for each of the 6,600 messages being monitored. Each probe pair is composed of a 25-mer oligonucleotide that is perfectly complementary to a region of sequence from a specific message, and a sister probe that is identical except for a single base substitution in a central position. This combination of perfect and mismatched probes serves as an internal control for hybridization specificity and allows for sensitive quantitation in the presence of cross-hybridization backgrounds. Probes were selected on the basis of uniqueness and hybridization specificity. The aim was to choose probes that would yield the best discrimination between perfect match and single base mismatch hybridization events.

Labeled RNAs for array hybridization experiments were derived from the malignant breast cell line BT-474 and normal primary breast tissue cell line HT-125. BT-474 was isolated from a solid, invasive ductal carcinoma of the breast and is tumorigenic in athymic nude mice, as described in Lasfargues, E. Y., Coutinho, W. G. & Redfield, E. S. Isolation of two human tumor epithelial cell lines from solid breast carcinomas. Journal of the National Cancer Institute 4, 967–978 (1978), incorporated herein by reference. HT-125 was obtained from normal breast tissue peripheral to an infiltrating ductal carcinoma Hackett, A. J., Smith, H. S., Springer, E. L., Owens, R. B., Nelson-Rees, W. A., Riggs, J. L. & Gardner, M. B. Two syngeneic cell lines from human breast tissue: the aneuploid mammary epithelial (Hs578T) and the diploid myoepithelial (Hs578Bst) cell lines. Journal of the National Cancer Institute 6, 1795–1806 (1977). mRNA was isolated from normal and malignant cells and converted into double stranded cDNA (ds cDNA) using an oligo dT primer containing a T7 promoter sequence at its 5'-end (5). ds cDNA product (with T7 polymerase promoter sequence incorporated) served as template in an in vitro transcription (VT) reaction using T7 polymerase and biotinylated ribonucleotides. The biotinylated cRNA was then fragmented by heating and hybridized to the oligonucleotide arrays. After washing and then staining with streptavidin-phycoerythrin conjugate, hybridization patterns were visualized using an argon ion laser scanning confocal microscope. The fluorescence intensity images were processed and quantitated by GeneChip data analysis software.

Hybridization patterns of total message from normal and malignant breast cells to sets of 20 probe pairs from 1,650 gene sequences (one array of a set of 4 encompassing 6,600 human genes) were obtained. Clear examples of unchanged and altered patterns of gene expression can be observed by visual comparison of the fluorescence intensities of probes sets from these two samples. The quantitative analysis of hybridization patterns is based on the assumption that for a specific mRNA the perfect-matched (PM) probes will hybridize more strongly on average than their mis-matched (MM) partners. The average difference in intensity between PM and MM hybridization signals is computed together with the average of the logarithm of the PM/MM ratios for each probe set. These values are then used to determine the relative copy number of a detected message.

Figure 8A:
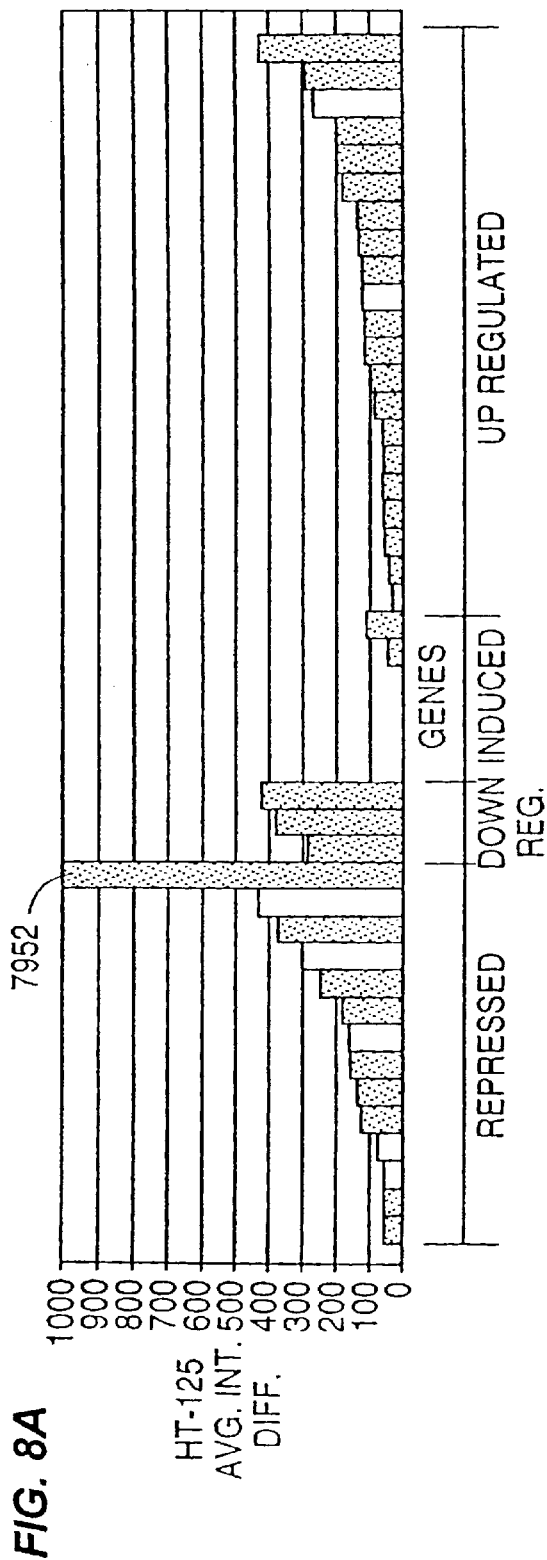
FIG. 8A and 8B illustrates expression profiles of subset of genes from normal versus malignant breast cells. Average perfect match-mismatch (PM-MM) intensity differences (normalized to β-Actin and GAPDH signals) were plotted for the genes that demonstrated greater than a 2-fold difference in hybridization signals between HT-125 and BT-474. Values for signals off scale are indicated.
Figure 8B:
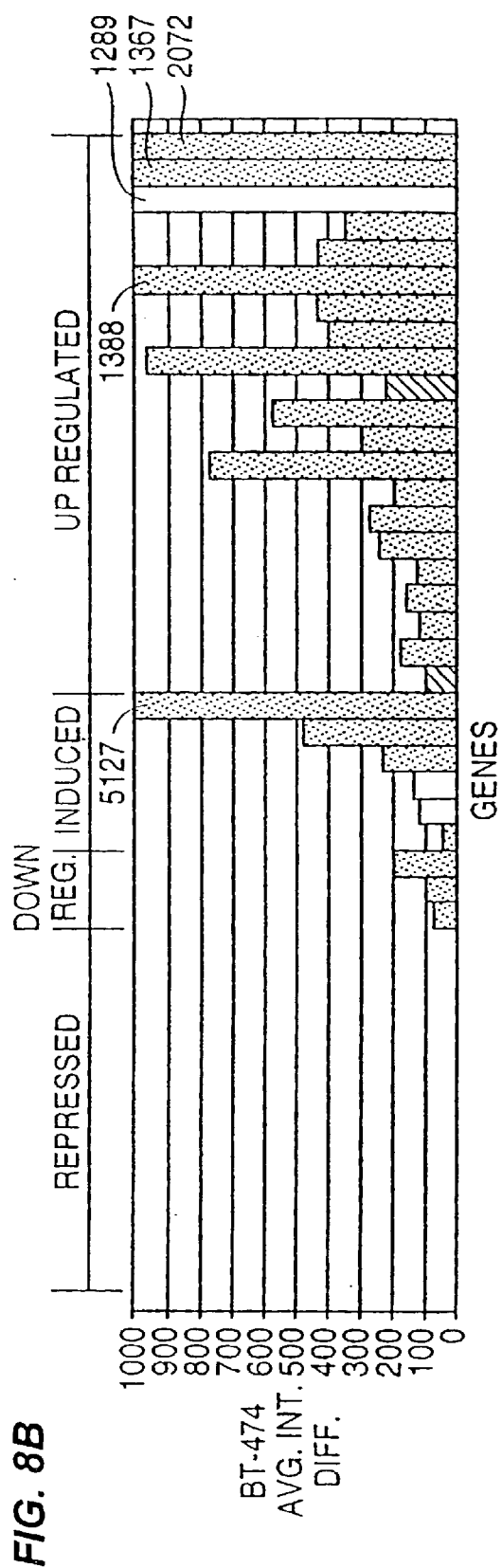
Figure 9A:
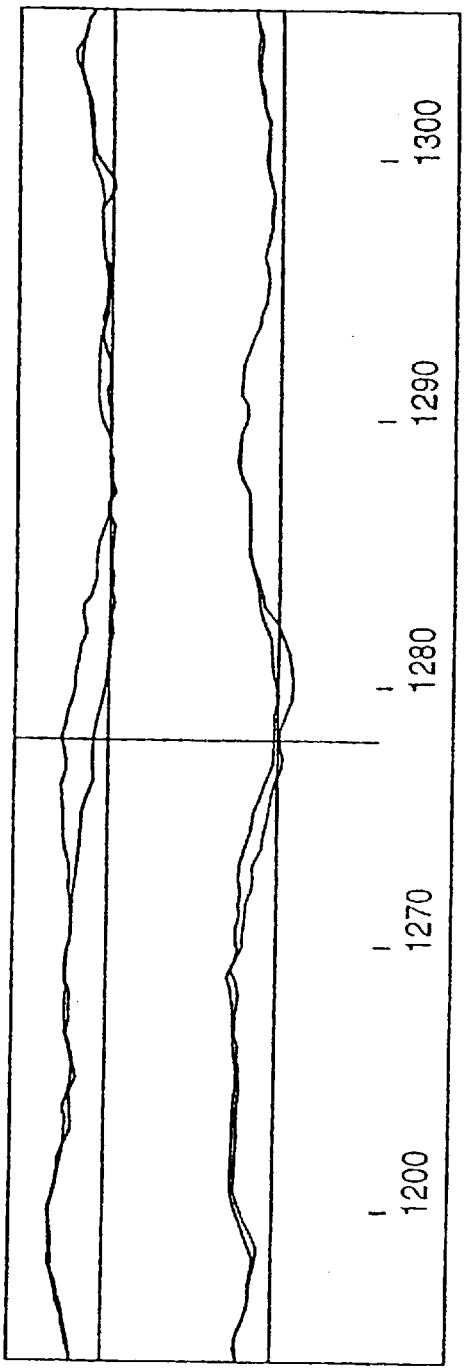
FIG. 9A, comparison of wild-type reference and BT-474 p53 gene hybridization intensity patterns from sense and anti-sense strands in the region containing a mutation. The area shown demonstrates the "footprint" and detection of a single-base difference between the samples. GeneChip data analysis output is shown (FIG. 9B) that unambiguously identifies a G→A base change at nucleotide 1,279 of p53 in BT-474 resulting in a glutamic acid to lysine amino acid change in exon 8 (DNA binding domain). The upper portion of output displays the p53 wild-type reference sequence. Aligned outputs of wild-type p53 control and BT-474 samples are shown.
Figure 9B:
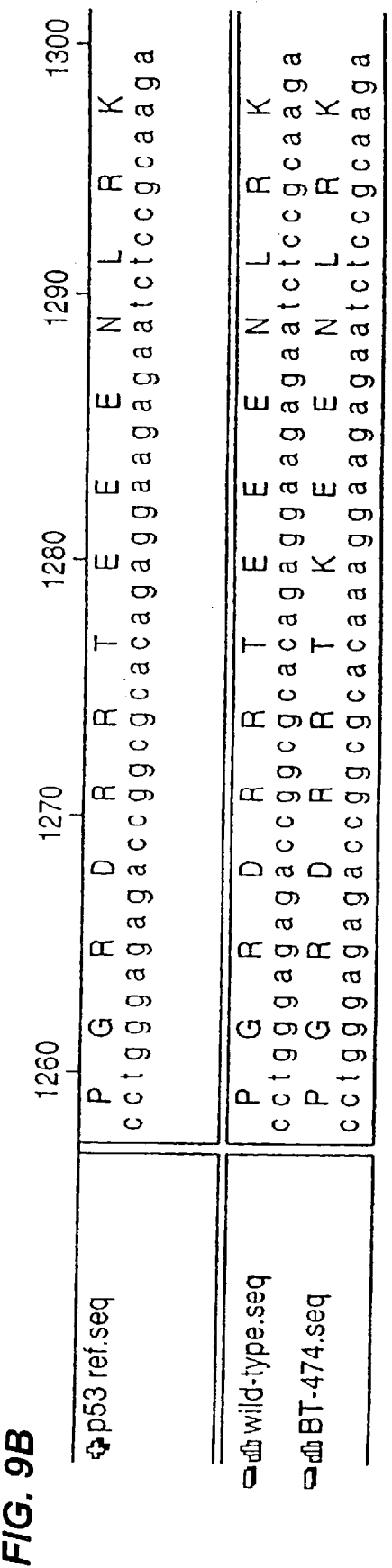

Added biotinylated control cRNAs (*E. coli* biotin synthetase genes bioB, bioC, bioD and bacteriophage P1 Cre recombinase) at known concentrations served as internal standards to allow relative quantitation of fluorescence intensities for estimates of copy number per cell. Spiking experiments were performed to investigate the absolute hybridization intensity range between multiple RNAs at known concentrations. When 32 individual cRNAs were spiked at levels ranging from copy numbers of 1:100,000 to 1:30,000 in the background of total cellular mRNA, absolute hybridization intensities were within a 2-fold range for all targets tested. Added biotinylated control oligonucleotide together with endogenous cellular RNA messages (e.g. β-Actin and glyceraldehyde 3-phosphate dehydrogenase (GAPDH)), allowed for normalization of experimental variation and array hybridization. Intensities from the spiked standards in the presence of total cellular target demonstrated sensitivities as high as 1:100,000, corresponding to a few copies per cell. Comparison of hybridization signal intensities, that range over 4-orders of magnitude, revealed all categories of message expression changes including repressed (>10-fold down), down-regulated (<10-fold down), up-regulated (<10-fold up) and induced (>10-fold up) mRNAs between normal and malignant cells as shown in FIG. 8A and 8B.

Genes that are repressed and induced/activated may provide a particularly good starting point to decipher the molecular pathways involved in programs of tumorigenesis. To identify the genes falling into each of these two categories we sorted the normal and malignant message populations to identify those genes that demonstrated a 10-fold or greater difference in messages intensities. This analysis revealed 168 genes repressed and 137 genes activated in BT-474 when compared to HT-125, as shown in Table 3 (FIG. 10A–10M). 260 of the messages displaying differential expression corresponded to Genflank human full length genes, 45 to ESTs with homologies to other eukaryotic or viral genes.

One of the largest changes observed in the activated group was the Her2/neu protooncogene (also known as c-erbB-2) which demonstrated a ~50-fold increase in BT-474 versus normal breast cells (5,127 versus 111 normalized fluorescence intensity units, see FIG. 1B). BT-474 tumor cells have been previously demonstrated to overexpress Her2/neu, as discussed in Styles, J. M., Harrison, S., Gusterson, B. A. & Dean, C. J. Rat monoclonal antibodies to the external domain of the product of the c-erbB-2 proto-oncogene, *International Journal of Cancer*, 2, 320–324 (1990), which belongs to the epidermal growth factor receptor family of receptor tyrosine kinases (RTKs), as discussed in Coussens, L., Yang-Feng, T. L., Liao, Y. C., Chen, E., Gray, A., McGrath, J., Seeburg, P. H., Libermann, T. A., Schlessinger, J., Francke, U., et al. Tyrosine kinase receptor with extensive homology to EGF receptor shares chromosomal location with neu oncogene, *Science* 4730, 1132–1139 (1985). The oncogenic activation of RTKs is commonly achieved by overexpression resulting in the ability to dimerize in the absence of ligand, as discussed in Earp, H. S., Dawson, T. L., Li, X. & Yu, H. Heterodimerization and functional interaction between EGF receptor family members: a new signaling paradigm with implications for breast cancer research, *Breast Cancer Research and Treatment* 1,115–132 (1995), and specifically, overexpression of Her2/neu is observed in 20–30% of all human breast cancers and ovarian cancers, as discussed in Earp, H. S., Dawson, T. L., Li, X. & Yu, H. Heterodimerization and functional interaction between EGF receptor family members: a new signaling paradigm with implications for breast cancer research, *Breast Cancer Research and Treatment* 1, 115–132 (1995); King, C. R., Kraus, M. H. & Aaronson, S. A. Amplification of a novel v-erbB-related gene in a human mammary carcinoma, *Science* 4717, 974–976 (1985); Slamon, D. J., Clark, G. M., Wong, S. G., Levin, W. J., Ulirich, A. & McGuire, W. L. Human breast cancer: correlation of relapse and survival with amplification of the HER-2/neu oncogene. *Science* 4785, 177–182 (1987); and Slamon, D. J., Godolphin, W., Jones, L. A., Holt, J. A., Wong, S, G., Keith, D. E., Levin, W. J, Stuart, S. G., Udove, J., Ullrich, A., et al. Studies of the HER-2/neu proto-oncogene in human breast and ovarian cancer, *Science* 4905, 707–712 (1989). Elevated expression of related RTK family member Her3 (c-erbB-3) has also been implicated in the development and progression of human malignancies including breast cancer as discussed in Kraus, M. H., Issing, W., Miki, T., Popescu, N. C. & Aaronson, S. A. Isolation and characterization of ERBB3, a third member of the ERBB/epidermal growth factor receptor family: evidence for overexpression in a subset of human mammary tumors, *Proceedings of the National Academy of Sciences of the United States of America* 23, 9193–9197 (1989), and Lemoine, N. R., Barnes, D. M., Hollywood, D. P., Hughes, C. M., Smith, P., Dublin, E., Prigent, S. A., Gullick, W. J. & Hurst, H. C. Expression of the ERBB3 gene product in breast cancer, *British Journal of Cancer* 6, 1116–1121 (1992). Consistent with these observations, significant levels of Her3 message were also detected in BT474 (undetectable in HT-125 versus 602 normalized fluorescence intensity units in BT474, see Table 1). Taken together, these data strongly implicate an involvement of RTKs and RTK heterodimerization in the development of this breast carcinoma; see Wallasch, C., Weiss, F. U., Niederfellner, G., Jallal, B., Issing, W. & Ullrich, A. Heregulin-dependent regulation of HER2/neu oncogenic signaling by heterodimerization with HER3, *EMBO J.* 14, 4267–4275 (1995). Underscoring the activated signal transduction pathway of RTKs was the also observed upregulation of GRB-7 (Table 1). GRB-7 is an SH2 domain protein and component of RTK signal transduction pathways that is overexpressed and found in tight complex with Her2/neu in certain breast cancers, as discussed in Stein, D., Wu, J., Fuqua, S. A., Roonprapunt, C., Yanjni, V., D'Eustachio, P., Moskow, J. J., Buchberg, A. M., Osborne, C. K. & Margolis, B. The SH2 domain protein GRB-7 is co-amplified, overexpressed and in tight complex with HER2 in breast cancer, *EMBO J.* 13, 1331–1340 (1994).

Prominent down-regulation of expression was observed for ~2.5% of the genes analyzed, with a dramatic loss of message levels seen for caveolin-1 and caveolin-2 genes (Table 1). Caveolins are integral membrane proteins and principle components of caveolae (non-clathrin-coated invaginations of the plasma membrane, as discussed in Lisanti, M. P., Tang, Z., Scherer, P. E., Kubler, E., Koleske, A. J. & Sargiacomo, M. Caveolae, transmembrane signalling and cellular transformation. *Molecular Membrane Biology*, 1, 121–124 (1995)). Recent evidence suggest that caveolae are involved in G protein-coupled (GPCR) signaling events, and specifically, that caveolins interact directly with multiple G protein α subunits to negatively regulate the activation state of heterotrimeric G proteins; see Lisanti, M. P., Tang, Z., Scherer, P. E., Kubler, E., Koleske, A. J. & Sargiacomo, M. Caveolae, transmembrane signalling and cellular transformation. *Molecular Membrane Biology*, 1, 121–124 (1995); Li, S., Okamoto, T., Chun, M., Sargiacomo, M., Casanova, J. E., Hansen, S. H., Nishimoto, I. & Lisanti, M. P. Evidence for a regulated interaction between heterotrimeric G proteins and caveolin, *Journal of Biological Chemistry* 26, 15693–15701 (1995). This proposed function is consistent with observations of reduced levels of caveolins in oncogenically transformed cells (Koleske, A. J., Baltimore, D. & Lisanti, M. P. Reduction of caveolin and caveolae in oncogenically transformed cells, *Proceedings of the National Academy of Sciences of the United States of America* 5, 1381–1385 (1995)) as well as results herein.

Ras proteins have been established as critical intermediates between upstream RTKs (21,22) and GPCRs (23,24), and downstream signaling components involved in cellular transformation (including mitogen activated protein (MAPK) kinases); see Van Biesen, T., Hawes, B. E., Luttrell, D. K., Krueger, K. M., Touhara, K., Porfiri, E., Sakaue, M., Luttrell, L. M. & Lefkowitz, R. J. Receptor-tyrosine-kinase- and G beta gamma-mediated MAP kinase activation by a common signalling pathway, *Nature* 6543, 781–784 (1995); Li, N., Batzer, A., Daly, R., Yajnik, V., Skolnik, E., Chardin, P., Bar-Sagi, D., Margolis, B. & Schlessinger, J. Guanine-nucleotide-releasing factor hSos1 binds to Grb2 and links receptor tyrosine kinases to Ras signalling, *Nature* 6424, 85–88 (1993); Howe, L. R., Marshall & C. J. Lysophosphatidic acid stimulates mitogen-activated protein kinase activation via a G-protein-coupled pathway requiring p21ras and p74raf-1. *Journal of Biological Chemistry* 28, 20717–20720 (1993); and Alblas, J., Van Corven, E. J., Hordijk, P. L., Milligan, G. & Moolenaar, W. H. Gi-mediated activation of the p21ras-mitogen-activated protein kinase pathway by alpha 2-adrenergic receptors expressed in fibroblasts. *Journal of Biological Chemistry* 30, 22235–22238 (1993). Although Ras mutations are seen in less than 5% of breast cancers, a large body of evidence implicates deregulation of the Ras pathway in breast carcinomas (Clark G. J. & Der, C. J. Aberrant function of the Ras signal transduction pathway in human breast cancer, *Breast Cancer Research and Treatmnent* 1, 133–144 (1995)). The concurrent up-regulation of RTKs and down-regulation of caveolins in BT474 strongly indicate a convergence of multiple upstream mitogenic signaling events on the Ras pathway in this breast carcinoma. Interestingly, our analysis also revealed up-regulation of Ras, Raf, Mek and ERK (Table 1) which together highlight a deregulated Ras/MAPK pathway; see Marshall, M. S. Ras target proteins in eukaryotic cells, *Faseb Journal* 13, 1311–1318 (1995), and Seger, R. & Krebs, E. G. The MAPK signaling cascade, *Faseb Journal* 9, 726–735 (1995). Collectively, these data elucidate a program of gene expression responsible for uncontrolled cell-cycle proliferation.

Further insights into the genetic defects of the BT-474 carcincoma came from the expression patterns of genes normally under the control of p53 transcriptional regulation. p53 is the most commonly mutated gene associated with neoplasia and mutations are found in over 50% of all human cancers. The p53 gene product is a nuclear phosphoprotein that functions in cell-cycle regulation and the preservation of genetic integrity (reviewed in Levine, A. J. p53, the cellular gatekeeper for growth and division. *Cell* 3, 323–331 (1997)). It possesses numerous biochemical properties necessary to carry out these functions, including sequence-specific DNA binding activity, transcriptional activation and transcriptional repression. The observation that p53 mutations found in human cancers overwhelmingly select for p53 gene products that have lost the ability to bind DNA and transcriptionally regulate target genes, strongly suggest that these properties are crucial in p53's regulation of cell proliferation and apoptosis.

Wild-type p53 protein transcriptionally activates a number of known genes that are linked with its tumor-suppressor activity and are responsible in part for p53-dependent functions in a cell. The mRNA levels of many of these target genes were detected in normal breast cells but were undetectable or dramatically down-regulated in the BT474 carcinoma (Table 2.) In addition, significant up-regulation of mRNAs in BT-474 that are normally transcriptionally repressed by wild-type p53 activity is observed (see Table 2); see Velculescu, V. E. & El-Deiry, W. S. Biological and clinical importance of the p53 tumor suppressor gene, *Clinical Chemistry* 6 Pt 1, 858–68 (1996). Taken together, these expression profiles indicated a loss of wild-type p53 function in these cells.

To investigate the cause of the transcriptionally inactive p53, genomic p53 was resequenced in BT474. The strategy for rapid, simultaneous analysis of large amounts of genetic information using high-density oligonucleotide arrays has been described in Chee, M., Yang, R., Hubbell, E., Berno, A., Huang, X. C., Stern, D., Winkler, I., Lockhart, D. J., Morris, M. S. & Fodor, S. P. Accessing genetic information with high-density DNA arrays, *Science* 5287, 610–614 (1996). The DNA array used in this study allowed for simultaneous analysis of both sense and anti-sense sequence of p53 coding exons 2–11, including 10 base pairs of intronic flanking sequence (to identify splice donor-acceptor mutations), as well as allele specific probes for over 300 characterized hotspot p53 mutations and every possible single base deletion (Dee et al., manuscript in prep.) The re-sequence analysis portion of the DNA array consisted of a set of 4 identical 20-mer oligonucleotides complementary to p53 wild-type sequence, except that an A, C, G or T was substituted into each probe at a centrally localized position. In each set of four probes, the perfect complement to the target sequence will hybridize more strongly than the single base mismatched probes (see FIG. 3A, wild-type), allowing unambiguous sequence assignment by automated basecalling software (30). By usingsets of 4 probes in this manner that span 1,490 bp of the p53 sequence, a single person can fully genotype the p53 gene from 60 genomes in the time it would take to do 12 by conventional gel-based de novo sequencing.

To facilitate characterization of mutations in the p53 gene we applied an algorithm that performs base identification of nucleotide changes between a sample and a reference. This sequence analysis is based on two major effects that a single base change has on the array hybridization pattern of an experimental sample relative to a wild-type reference: 1) The probe containing the substitution base displays the strongest signal of the 4 probe set; and 2) The neighboring probes that overlap the position display a characteristic loss of signal or "footprint" for probes flanking a base substitution, as these probes would have a single base mismatch to the mutated target sequence distinct from the query base (see FIG. 3A, BT-474 versus wild-type, and ref. 30).

The analysis of BT-474 versus HT-125 p53 genomic DNA using the p53 genotyping array revealed a single base substitution of G to A in exon 8 (DNA binding domain), resulting in an amino acid change at position 285 from E to K (FIG. 3B). The hybridization signal difference centered about the mutation identified by the footprint analysis (see FIG. 3B, top panel), and subsequent base calling of a single genotype (see FIG. 3B, bottom panel) in BT-474 by the GeneChip software indicated that this carcinoma had a loss of heterozygosity at the p53 locus (confirmed by dideoxy sequence analysis). These data unambiguously show that the loss of wild-type p53 transcriptional function in these cells was due to the absence of wild-type p53 protein. We have applied this analysis to other breast carcinomas with similar outcomes correlating altered gene expression patterns of targets of p53 transcriptional modulation with mutant p53 gene status (Table 3).

Systematic expressed genome sequencing is producing EST data at a rate that predicts ESTs to all human genes will be available in just a few years. To fully exploit the expressed sequence database, an understanding of gene function from gene sequence is required. Oligonucleotide arrays can provide a basis for genome-wide expression analysis and offer insights into regulatory interactions and gene function.

Experimental

Cell Culture

BT-474, MDA468 and MDA231 cells were maintained in RPMI-1640 (Gibco/BRL) containing 10% Fetal Bovine Serum, 10 µg/ml bovine insulin, 2 mM glutamine, 100 units/ml Penicillin and 100 µg/ml Streptomycin. HT-125 cells were maintained in Modified Dulbecco's Medium (Gibco/BRL) with 10% Fetal Bovine Serum, 30 ng/ml epidermal growth factor, 10 µg/ml bovine insulin, 10 µM non-essential amino acids, 100 units/ml Penicillin and 100 µg/ml Streptomycin. Cell lines were kept at 37° C., 5% $CO_2$ and split 1 to 3 at approximately 60–70% confluency.

mRNA Preparation and Labeling for Gene Expression Monitoring

Poly $A^+$ RNA was isolated from cells using an Oligotex Direct mRNA Kit (Qiagen) following both standard and batch protocols according to the manufacturer's instructions. 0.5–1 µg of mRNA was then converted into ds cDNA using a Superscript Choice System cDNA Synthesis Kit (Gibco/BRL) and an oligo dT primer incorporating a T7 RNA polymerase promoter sequence on its 5'-end. The resultant ds cDNA was purified by one step of phenol/chloroform extraction using Phase Lock Gel (5 Prime to 3 Prime) followed by EtOH precipitation. The ds cDNA product then served as target in an in-vitro transcription labeling reaction using T7 RNA polymerase (Ambion T7 Megascript Transcription Kit), 1.875 mM biotin-CTP and 1.875 mM biotin-UTP for a final concentration of 7.5 mM each NTP. After a 6 hour incubation at 37° C., the total labeled cRNA transcripts were purified by Chromaspin-100 columns (Clontech), followed by ProCipitate treatment (Affinity Binding) and EtOH precipitation to remove unincorporated nucleotides and protein contaminants.

Gene Expression Array Hybridization and Scanning

10 µg of biotinylated cRNA target was fragmented to an average size of 50 nucleotides in 10 µl of magnesium fragmentation buffer (40 mM Tris-acetate (pH 8.1), 100 mM KOAc, 30 mM MgOAc) at 95° C. for 35 min. The fragmented samples were brought up to a final volume of 200 µl with hybridization buffer (0.9 M NaCl, 60 mM $NaH_2PO_4$, 6 mM EDTA and 0.005% Triton X-100, pH 7.6 (6×SSPE-T)) containing 0.1 ng/ml Herring Sperm DNA, 50 pM biotin-labeled control oligo (5'-GTCAAGATGCTACCGTTCAG-3') and biotinylated cRNA quantitation standards bioB (1.5 pM), bioC (5.0 pM), bioD (25 pM) and Cre (100 pM). Samples were denatured at 95° C. for 10 min, chilled on ice for 5 min and equilibrated to room temperature (5 min) before being applied to the array flow cell. Arrays were hybridized at 40° C. for 14–16 hr with rotation at 60 rpm, followed by 10 wash cycles (2 drain-fills/cycle) at room temperature with 6×SSPE-T in the GeneChip Fluidics Station (RELA). For staining of hybridized target cRNA, arrays were first washed in 0.5×SSPE-T at 40° C. for 15 min with rotation (60 rpm), then incubated with 2 µg/ml of phycoerytherin-strepavidin conjugate (Molecular Probes) in 6×SSPE-T containing 1 mg/ml of acetylated-bovine serum albumin at 40° C. for 10 min. Prior to scanning, the arrays were washed at room temperature with 6×SSPE-T for 5 cycles (2 drains-fills/cycle) in the fluidics station. The hybridized stained arrays were scanned using an argon-ion laser GeneChip scanner 50 (Molecular Dynamics) with a resolution setting of 7.5 µm/pixel (~45 pixels/probe cell), and wavelength detection setting of 560 nm. Fluorescence images and quantitative analysis of hybridization patterns and intensities were performed using GeneSeq Analysis Software and GEprocess (Affymetrix) gene expression data analysis programs.

p53 PCR and Labeling for Re-sequence Analysis by Array Hybridization

The p53 gene was genotyped by amplifying coding exons 2–11 in a 100 µl multiplex PCR reaction using 100 ng of genomic DNA extracted from cells using a QIAmp Blood Kit (Qiagen). PCR Buffer II (Perkin-Elmer) was used at 1× along with 2.5 mM $MgCl_2$, 200 µM of each dNTP and 10 units of Taq Polymerase Gold (Perkin-Elmer). The multiplex PCR was performed using 10 exon-specific primers (Table 4) with the following cycling conditions: 1 cycle at 94° C. (5 min), 50 cycles of 94° C. (30 sec), 60° C. (30 sec) and 72° C. (30 sec), followed by 1 cycle at 72° C. (7 min). 45 µl of the PCR reaction was then fragmented and dephosphorylated by incubation at 25° C. for 15 min with 0.25 units of Amp Grade DNAse I (Gibco/BRL) and 2.5 units of Calf Alkaline Phosphatase (Gibco/BRL), followed by heat-inactivation at 99° C. for 10 min. The fragmented PCR products were then labeled in a 100 µl reaction using 10 µM flourecein-N6-ddATP (Dupont-NEN) and 25 units of terminal transferase (Boehringer Mannheim) in 200 µM K-Cacodylate, 25 mM Tris-HCl (pH 6.6), 0.25 mg/ml BSA and 2.5 mM $CoCl_2$. The labeling reaction was incubated at 37° C. for 45 min and heat-inactivated at 99° C. for 5 min.

p53 Re-sequence Analysis Array Hybridization and Scanning

The fragmented, labeled PCR reaction was hybridized to the p53 re-sequence analysis array in 6×SSPE-T containing 2 mg/ml BSA and 1.67 nM fluorescein-labeled control oligo (5'-CTGAACGGTAGCATCTTGAC-3') at 45° C. for 30 min. The array was then washed with 3×SSPE-T at 35° C. for 4 cycles (10 drains-fills/cycle) in the GeneChip Fluidics Station (RELA). The hybridized p53 array was scanned using an argon-ion laser scanner (Hewlett-Packard) with a resolution setting of 6.0 µm/pixel (~70 pixels/probe cell) and wavelength detection setting of 530 nm. A fluorescence image was created, intensity information analyzed and nucleotide determination made by GeneChip Analysis Software (Affymetrix). Footprint analysis was done using Ulysses Analysis Software (Affymetrix) essentially as described.

Genotyping Through-put Capabilities

Conventional gel-based dideoxynucleotide sequencing can genotype approximately twelve p53 genomes a day (10 hr) assuming an average read of 400 nucleotides per gel, run twice a day. The through-put of the GeneChip p53 system for a single person, using one fluidics station and scanner (40 min hyb/wash and 6 min scan time) is approximately 6 arrays per hour, or sixty p53 genomes fully genotyped in a 10 hour period.

Gene Expression Array Oligonucleotide Probe Selection and Array Desgin

The probes for the human 6,600 gene arrays were selected from the 600 bases at the 3'-end of sequences chosen from the dbEST database. Probes for inclusion on the arrays were identified based on a criteria of uniqueness and hybridization characteristics. Uniqueness was accessed by comparing potential probes with all genes that were considered for inclusion on the arrays. If any potential probe matched 22 out of 25 nucleotides of another sequence that probe was discarded. Selection of probes for hybridization characteristics was done by using heuristic rules and a neural net developed from previous expression experiments. The heuristics for the 6,600 gene arrays were as follows: 1) total number of As or Ts less than 13; 2) total number of Cs or Gs less than 11; 3) number of As or Ts in a window of 8 less than 7; 4) number of Cs or Gs in a window of 8 less than 6; 5) palindrome score less than 9 (the palindrome score is a measure of probe self-complementarity). The neural net was used to prune out probes that it identified as poor hybridizers or promiscuous cross hybridizers as described in detail elsewhere. Finally, any probes requiring more than 70 synthesis steps to include on the arrays were rejected to minimize synthesis time and cost.

Data from tables 2 & 3 include expression results from an array designed to identify alternatively spliced forms of targets. This array surveys 250 genes from functional categories including oncogene, tumor suppressor, DNA mismatched repair and apoptosis gene products. Probe pairs for this design were chosen such that each exon for a given message was represented on the array. In this way, specific loss of signal from a sub-set of probes corresponding to a particular exon of a message would indicate a splice variant form.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

Conclusion

The present invention provides greatly improved methods, compositions, and apparatus for identifying gene function and for studying the regulatory relationship among genes. It is to be understood that the above description is intended to be illustrative and not restrictive. Many variations of the invention will be apparent to those of skill in the art upon reviewing the above description. By way of example, the invention has been described primarily with reference to the use of a high density oligonucleotide array, but it will be readily recognized by those of skill in the art that other nucleic acid arrays, other methods of measuring transcript levels and gene expression monitoring at the protein level could be used. The scope of the invention should, therefore, be determined not with reference to the above description, but should instead be determined with reference to the appended claims, along with the full scope of equivalents to which such claims are entitled.

We claim:

1. A method for detecting a functional mutation in a target up-stream regulatory gene comprising:
   preparing a reference sample from reference cells having a wild-type up-stream regulatory gene corresponding to said target up-stream regulatory gene;
   preparing a target sample from target cells suspected of having a mutation in said target up-stream regulatory gene, said target cells being otherwise substantially similar to said reference cells;
   detecting the expression of a plurality of down-stream genes in said reference sample to obtain a reference expression pattern, said down-stream genes being up or down regulated by said wild-type up-stream regulatory gene;
   detecting the expression of said plurality of down-stream genes in said target sample to obtain a target expression pattern; and
   comparing said reference expression pattern with said target expression pattern to detect functional mutation in or inactivation of said target gene.

2. The method of claim 1, wherein said down-stream genes are transcriptionally regulated by said wild-type up-stream regulatory gene and said reference and target expression patterns are detected by measuring the amount of transcripts of said down-stream genes in said reference and target samples.

3. The method of claim 2, wherein said amount of transcripts is detected with a high density nucleic acid array.

4. The method of claim 1, wherein said reference and target expression patterns are detected by measuring the amount of protein products of said down-stream genes in said reference and target samples.

5. The method of claim 1 further comprising the steps of:
   detecting expression of a plurality of control genes in said reference and target samples, said control genes being unresponsive to the function of said up-stream regulatory gene; and
   comparing reference and target expression patterns of control genes to provide a baseline for detecting a significant difference in expression patterns.

6. The method of claim 1 further comprising the step of:
   indicating a loss of wild-type function in said target gene if a significant number of said down regulated genes are expressed relatively higher in said target sample than in said reference sample or if a significant number of said up-regulated genes are expressed lower in said target sample than in said reference sample.

7. The method of claim 1 further comprising the step of:
   indicating a gain of function mutation in said target gene if a significant portion of said down regulated genes are expressed lower in said target sample than in said reference sample or if a significant portion of said up-regulated genes are expressed higher in said target sample than in said reference sample.

8. A method for detecting a p53 gene functional mutation in target cells comprising the steps of:
   preparing a reference sample from reference cells having a wild-type p53 gene, said reference cells being otherwise substantially similar to said target cells;
   detecting the expression of a plurality of more than 100 down-stream genes in said reference cells and said target cells to obtain a target expression pattern and a reference expression pattern, said down-stream genes being up- or down-regulated by said wild-type p53 gene; and
   comparing said reference expression pattern with said target expression pattern to detect said p53 functional mutation.

9. The method of claim 8, wherein said down-stream genes are transcriptionally regulated by said wild-type p53 gene and the expression of said down-stream genes is detected by measuring the amount of transcripts of said down-stream genes in said reference and target cells.

10. The method of claim 9, wherein said amount of transcripts is measured with high density nucleic acid array.

11. The method of claim 9, wherein said down-stream genes comprise p53 up-regulated gadd45, cyclin G, p21waf1, Bax, IGF-BP3 and Thrombospondin genes and p53 down-regulated c-myc and PCNA genes.

12. An in-cell functional assay for a p53 sequence alteration comprising the steps of:

preparing a target sample from target cells having said p53 sequence alteration;

preparing a reference sample from reference cells having a wild-type p53 gene, said reference cells being otherwise substantially similar to said target cells;

detecting the expression of a plurality of more than 100 down-stream genes in said reference cells to obtain a reference expression pattern and in said target cells to obtain a target expression pattern, said down-stream genes being selected from the group consisting of p53 up-regulated genes and p53 down-regulated genes; and comparing said reference expression pattern with said target expression pattern to determine the function of said p53 sequence alteration.

13. The method of claim 12, wherein said down-stream genes are transcriptionally regulated by said wild-type p53 gene and the expression of said down-stream genes is detected by measuring the amount of transcripts of said down-stream genes in said reference and target cells.

14. The method of claim 13, wherein said amount of transcripts is measured with a high density nucleic acid array.

15. The method of claim 13, wherein said down-stream genes comprise p53 up regulated gadd45, cyclin G, p21waf1, Bax, IGF-BP3 and Thrombospondin genes and p53 down regulated c-myc and PCNA genes.

* * * * *

SEQUENCE LISTING

<160> NUMBER OF SEQ ID NOS: 6

<210> SEQ ID NO 1
<211> LENGTH: 14
<212> TYPE: PRT
<213> ORGANISM: Homo sapiens

<400> SEQUENCE: 1

Pro Gly Arg Asp Arg Arg Thr Glu Glu Glu Asn Leu Arg Lys
 1               5                  10

<210> SEQ ID NO 2
<211> LENGTH: 43
<212> TYPE: DNA
<213> ORGANISM: Homo sapiens

<400> SEQUENCE: 2
cctgggagag accggcgcac agaggaagag aatctccgca aga          43

<210> SEQ ID NO 3
<211> LENGTH: 14
<212> TYPE: PRT
<213> ORGANISM: Homo sapiens

<400> SEQUENCE: 3

Pro Gly Arg Asp Arg Arg Thr Glu Glu Glu Asn Leu Arg Lys

-continued

```
<210> SEQ ID NO 4
<211> LENGTH: 43
<212> TYPE: DNA
<213> ORGANISM: Homo sapiens

<400> SEQUENCE: 4
cctgggagag accggcgcac agaggaagag aatctccgca aga                43

<210> SEQ ID NO 5
<211> LENGTH: 14
<212> TYPE: PRT
<213> ORGANISM: Homo sapiens

<400> SEQUENCE: 5

Pro Gly Arg Asp Arg Arg Thr Lys Glu Glu Asn Leu Arg Lys
 1               5                  10

<210> SEQ ID NO 6
<211> LENGTH: 43
<212> TYPE: DNA
<213> ORGANISM: Homo sapiens

<400> SEQUENCE: 6
cctgggagag accggcgcac aaaggaagag aatctccgca aga                43
```